United States Patent
Miodragovic et al.

(10) Patent No.: US 9,499,574 B2
(45) Date of Patent: Nov. 22, 2016

(54) ARSENOPLATIN ANTI-CANCER AGENTS

(71) Applicant: Northwestern University, Evanston, IL (US)

(72) Inventors: Denana U. Miodragovic, Chicago, IL (US); Thomas V. O'Halloran, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/421,982

(22) PCT Filed: Aug. 14, 2013

(86) PCT No.: PCT/US2013/054999
§ 371 (c)(1),
(2) Date: Feb. 16, 2015

(87) PCT Pub. No.: WO2014/028653
PCT Pub. Date: Feb. 20, 2014

(65) Prior Publication Data
US 2015/0218195 A1    Aug. 6, 2015

Related U.S. Application Data

(60) Provisional application No. 61/683,031, filed on Aug. 14, 2012.

(51) Int. Cl.
| | |
|---|---|
| C07F 19/00 | (2006.01) |
| C07F 15/00 | (2006.01) |
| C07F 15/04 | (2006.01) |
| C07F 9/90 | (2006.01) |
| C07F 9/94 | (2006.01) |
| C07F 9/70 | (2006.01) |

(52) U.S. Cl.
CPC ............. *C07F 19/005* (2013.01); *C07F 9/70* (2013.01); *C07F 9/902* (2013.01); *C07F 9/94* (2013.01); *C07F 15/0013* (2013.01); *C07F 15/0066* (2013.01); *C07F 15/045* (2013.01)

(58) Field of Classification Search
CPC ........ C07F 19/005; C07F 9/70; C07F 9/902; C07F 9/94; C07F 15/045; C07F 15/0013; C07F 15/0066
See application file for complete search history.

(56) References Cited

U.S. PATENT DOCUMENTS

2004/0258759 A1   12/2004 Suslick et al.

FOREIGN PATENT DOCUMENTS

| | | |
|---|---|---|
| CA | 1196004 | 10/1985 |
| CN | 101434622 | 5/2009 |
| EP | 0306605 | 3/1989 |

OTHER PUBLICATIONS

Miodragovic et al, Angewandte Chemie, International Edition (2013), 52(41), 10749-10752.*
International Search Report dated Nov. 13, 2013.
Anderson et al., "An expanded genetic code with a functional quadruplet codon," Proc. Natl. Acad. Sci. U.S.A. 101(20):7566-7571 (2004).
Bacher et al., "Selection and Characterization of *Escherichia coli* Variants Capable of Growth on an Otherwise Toxic Tryptophan Analogue," J. Bacteriol. 183(18):5414-5425 (2001).
Budisa et al., "Proteins with (beta)-(thienopyrrolyl)alanines as alternative chromophores and pharmaceutically active amino acids," Protein Sci. 10(7):1281-1292 (2001).
Chin et al., "An Expanded Eukaryotic Genetic Code," Science 301(5635):964-967 (2003).
Hamano-Takaku et al., "A Mutant *Escherichia coli* Tyrosyl-tRNA Synthetase Utilizes the Unnatural Amino Acid Azatyrosine More Efficiently than Tyrosine," J. Biol. Chem. 275(51):40324-40328 (2000).
Ibba et al., "Genetic code: introducing pyrrolysine," Curr Biol. 12(13):R464-R466 (2002).
Ikeda et al., "Synthesis of a novel histidine analogue and its efficient incorporation into a protein in vivo," Protein Eng. Des. Sel. 16(9):699-706 (2003).
James et al., "Kinetic characterization of ribonuclease S mutants containing photoisomerizable phenylazophenylalanine residues," Protein Eng. Des. Sel. 14(12):983-991 (2001).
Stadtman, "Selenocysteine," Annu Rev Biochem. 65:83-100 (1996).
Stryer et al., Biochemistry, 5.sup.th ed., Freeman and Company (2002).
Zhang et al., "Selective incorporation of 5-hydroxytryptophan into proteins in mammalian cells," Proc. Natl. Acad. Sci. U.S.A. 101(24):8882-8887 (2004).

* cited by examiner

*Primary Examiner* — Sudhakar Katakam
(74) *Attorney, Agent, or Firm* — Klintworth & Rozenblat IP LLC

(57) ABSTRACT

Disclosed are compound having the structure of formula (I):

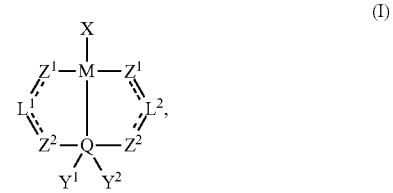

(I)

wherein M is Pt, Pd or Ni; Q is As, Sb or Bi; $Z^1$ is N; $Z^2$ is O or S; $L^1$ and $L^2$ are independently C(O), C—$R^1$ or C—$R^2$; X is a Lewis base and $Y^1$ and $Y^2$ are independently oxygen- or sulfur-containing substituents, conjugates containing compounds of formula (I) and their use as chemotherapy agents.

12 Claims, 8 Drawing Sheets

ARSENOPLATIN ANTI-CANCER AGENTS

CROSS-REFERENCE TO RELATED APPLICATIONS

The present application is the National Stage of International Application No. PCT/US2013/054999, filed Aug. 14, 2013, and entitled "ARSENOPLATIN ANTI-CANCER AGENTS," which claims the benefit of U.S. Provisional Application No. 61/683,031 filed Aug. 14, 2012, and entitled ARSENOPLATINS-A NEW CLASS OF ANTI-CANCER AGENTS." The content of the U.S. Provisional Patent Application is hereby incorporated by reference in its entirety.

STATEMENT REGARDING FEDERALLY SPONSORED RESEARCH OR DEVELOPMENT

This invention was made with government support under grant numbers U01 CA151461, U54 CA119341, U54 CA143869, P50 CA090386 awarded by the National Institutes of Health and grant number W81XWH-08-1-0672 awarded by the US Army Medical Research and Materiel Command. The government has certain rights in the invention.

BACKGROUND

1. Technical Field

The disclosure relates to arsenoplatin and related compounds and methods for their use as chemotherapy agents.

2. Description of Relevant Prior Art

Cis-diamminedichloroplatinum(II) ("Cisplatin") and arsenic trioxide ($As_2O_3$) are highly successful agents for treatment of cancer. Cisplatin is used in combination chemotherapy to treat ovarian, testicular, head, neck, and bladder cancers. Unfortunately, these and other cancers frequently develop resistance to this widely used agent and there are intensive efforts to develop new agents that overcome this resistance. Arsenic trioxide, which was discovered as a traditional Chinese medicine, is a front line treatment for acute promyelocytic leukemia and has also shown preliminary efficacy in the treatment of blood cancers such as multiple myeloma and myelodysplastic syndromes.

Both compounds induce apoptotic cell death, but through different pathways. Cisplatin reacts with DNA and causes intra- and inter-strand DNA cross-links. The principal component of aqueous solutions of $As_2O_3$ at pH 7, arsenous acid, at low concentrations reacts with and triggers degradation of key zinc-dependent regulatory proteins and inhibits angiogenesis, migration and invasion. At higher concentrations, arsenous acid triggers apoptosis through pathways that involve elevated levels of reactive oxygen species in mitochondria.

When combined, these agents can act synergistically in certain cisplatin sensitive and resistant ovarian and non-small lung carcinoma cells. The only example of a platinum adduct with arsenous acid in the literature emerged in efforts to develop efficient systems for loading $As_2O_3$ into liposomes with aquated forms of cisplatin.

BRIEF SUMMARY

In a first aspect, a compound having the structure of formula (I) is disclosed:

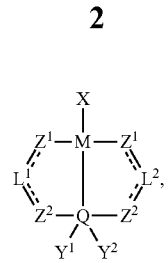

wherein M is Pt, Pd or Ni; Q is As, Sb or Bi; $Z^1$ is N; $Z^2$ is O or S; $L^1$ and $L^2$ are independently C(O), C—$R^1$ or C—$R^2$; X is a Lewis base; $Y^1$ and $Y^2$ are independently selected from —$OR^3$, —$OR^4$, —$SR^3$ and $SR^4$, wherein $R^1$ and $R^2$ are independently selected from hydrogen, halogen, cyano, keto, ester, ether, thiol, thioether, thioester, imino, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl, and $C_3$-$C_{15}$ heterocycloalkyl;

wherein $R^3$ and $R^4$ are independently selected from hydrogen, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl, and $C_3$-$C_{15}$ heterocycloalkyl;

wherein the Lewis base can be halogen, N-bonded cyano, nitroso, nitroxyl, N-bonded $C_1$-$C_{10}$ alkyl, $C_1$-$C_{10}$ alkenyl, N-bonded $C_3$-$C_{10}$ cycloalkyl, N-bonded $C_1$-$C_{10}$ heteroalkyl, N-bonded $C_1$-$C_{10}$ heteroalkenyl, N-bonded aryl, N-bonded heteroaryl, N-bonded $C_3$-$C_{15}$ heterocycloalkyl, $NR^5R^6$, N-bonded ligand, S-bonded cyano, sulfonyl, sulfoxyl, thiol, S-bonded thioether, S-bonded thioester, S-bonded $C_1$-$C_{10}$ alkyl, $C_1$-$C_{10}$ alkenyl, S-bonded $C_3$-$C_{10}$ cycloalkyl, S-bonded $C_1$-$C_{10}$ heteroalkyl, S-bonded $C_1$-$C_{10}$ heteroalkenyl, S-bonded aryl, S-bonded heteroaryl, S-bonded $C_3$-$C_{15}$ heterocycloalkyl, —$SR^5$, S-bonded ligand, O-bonded $C_3$-$C_{10}$ cycloalkyl, O-bonded $C_1$-$C_{10}$ heteroalkyl, O-bonded $C_1$-$C_{10}$ heteroalkenyl, O-bonded aryl, O-bonded heteroaryl, O-bonded $C_3$-$C_{15}$ heterocycloalkyl, —$OR^5$, O-bonded carboxylato, O-bonded polycarboxylato, O-bonded carboxylato, O-bonded polycarboxylato, O-bonded carboxylato, O-bonded polycarboxylato, O-bonded ligand, or P-bonded phosphine having formula $P(R^7)_{3-x}(R^8)_x$, where x is 0, 1, 2 or 3;

wherein $R^5$ and $R^6$ are independently selected from hydrogen, O, —$CO_2R^9$, —$COR^9$, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl;

wherein $R^7$ and $R^8$ are independently selected from $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl; and wherein $R^9$ is selected from hydrogen, hydroxyl, halogen, amine, thiol, ether, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl.

In a second aspect, conjugate that includes a ligand and a compound having the structure of formula (I) is disclosed:

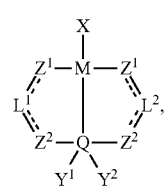

wherein M is Pt, Pd or Ni; Q is As, Sb or Bi; $Z^1$ is N; $Z^2$ is O or S; $L^1$ and $L^2$ are independently C(O), C—$R^1$ or C—$R^2$; X is a Lewis base; $Y^1$ and $Y^2$ are independently selected from —$OR^3$, —$OR^4$, —$SR^3$ and $SR^4$, wherein $R^1$ and $R^2$ are independently selected from hydrogen, halogen, cyano, keto, ester, ether, thiol, thioether, thioester, imino, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl, and $C_3$-$C_{15}$ heterocycloalkyl;

wherein $R^3$ and $R^4$ are independently selected from hydrogen, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl, and $C_3$-$C_{15}$ heterocycloalkyl;

wherein the Lewis base can be halogen, N-bonded cyano, nitroso, nitroxyl, N-bonded $C_1$-$C_{10}$ alkyl, $C_1$-$C_{10}$ alkenyl, N-bonded $C_3$-$C_{10}$ cycloalkyl, N-bonded $C_1$-$C_{10}$ heteroalkyl, N-bonded $C_1$-$C_{10}$ heteroalkenyl, N-bonded aryl, N-bonded heteroaryl, N-bonded $C_3$-$C_{15}$ heterocycloalkyl, $NR^5R^6$, N-bonded ligand, S-bonded cyano, sulfonyl, sulfoxyl, thiol, S-bonded thioether, S-bonded thioester, S-bonded $C_1$-$C_{10}$ alkyl, $C_1$-$C_{10}$ alkenyl, S-bonded $C_3$-$C_{10}$ cycloalkyl, S-bonded $C_1$-$C_{10}$ heteroalkyl, S-bonded $C_1$-$C_{10}$ heteroalkenyl, S-bonded aryl, S-bonded heteroaryl, S-bonded $C_3$-$C_{15}$ heterocycloalkyl, —$SR^5$, S-bonded ligand, O-bonded $C_3$-$C_{10}$ cycloalkyl, O-bonded $C_1$-$C_{10}$ heteroalkyl, O-bonded $C_1$-$C_{10}$ heteroalkenyl, O-bonded aryl, O-bonded heteroaryl, O-bonded $C_3$-$C_{15}$ heterocycloalkyl, —$OR^5$, O-bonded carboxylato, O-bonded polycarboxylato, O-bonded ligand, or P-bonded phosphine having formula $P(R^7)_{3-x}(R^8)_x$, where x is 0, 1, 2 or 3;

wherein $R^5$ and $R^6$ are independently selected from hydrogen, O, —$CO_2R^9$, —$COR^9$, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl;

wherein $R^7$ and $R^8$ are independently selected from $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl; and wherein $R^9$ is selected from hydrogen, hydroxyl, halogen, amine, thiol, ether, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl.

In a third aspect, a method of treating a cancer cell that includes the step of contacting the cancer cell with a compound having the structure of formula (I) is disclosed:

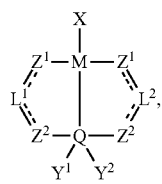

(I)

wherein M is Pt, Pd or Ni; Q is As, Sb or Bi; $Z^1$ is N; $Z^2$ is O or S; $L^1$ and $L^2$ are independently C(O), C—$R^1$ or C—$R^2$; X is a Lewis base; $Y^1$ and $Y^2$ are independently selected from —$OR^3$, —$OR^4$, —$SR^3$ and —$SR^4$, wherein $R^1$ and $R^2$ are independently selected from hydrogen, halogen, cyano, keto, ester, ether, thiol, thioether, thioester, imino, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl, and $C_3$-$C_{15}$ heterocycloalkyl;

wherein $R^3$ and $R^4$ are independently selected from hydrogen, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl, and $C_3$-$C_{15}$ heterocycloalkyl;

wherein the Lewis base can be halogen, N-bonded cyano, nitroso, nitroxyl, N-bonded $C_1$-$C_{10}$ alkyl, $C_1$-$C_{10}$ alkenyl, N-bonded $C_3$-$C_{10}$ cycloalkyl, N-bonded $C_1$-$C_{10}$ heteroalkyl, N-bonded $C_1$-$C_{10}$ heteroalkenyl, N-bonded aryl, N-bonded heteroaryl, N-bonded $C_3$-$C_{15}$ heterocycloalkyl, $NR^5R^6$, N-bonded ligand, S-bonded cyano, sulfonyl, sulfoxyl, thiol, S-bonded thioether, S-bonded thioester, S-bonded $C_1$-$C_{10}$ alkyl, $C_1$-$C_{10}$ alkenyl, S-bonded $C_3$-$C_{10}$ cycloalkyl, S-bonded $C_1$-$C_{10}$ heteroalkyl, S-bonded $C_1$-$C_{10}$ heteroalkenyl, S-bonded aryl, S-bonded heteroaryl, S-bonded $C_3$-$C_{15}$ heterocycloalkyl, —$SR^5$, S-bonded ligand, O-bonded $C_3$-$C_{10}$ cycloalkyl, O-bonded $C_1$-$C_{10}$ heteroalkyl, O-bonded $C_1$-$C_{10}$ heteroalkenyl, O-bonded aryl, O-bonded heteroaryl, O-bonded $C_3$-$C_{15}$ heterocycloalkyl, —$OR^5$, O-bonded carboxylato, O-bonded polycarboxylato, O-bonded ligand, or P-bonded phosphine having formula $P(R^7)_{3-x}(R^8)_x$, where x is 0, 1, 2 or 3;

wherein $R^5$ and $R^6$ are independently selected from hydrogen, O, —$CO_2R^9$, —$COR^9$, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl;

wherein $R^7$ and $R^8$ are independently selected from $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl; and wherein $R^9$ is selected from hydrogen, hydroxyl, halogen, amine, thiol, ether, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl.

In a fourth aspect, a pharmaceutical composition that includes an excipient and a compound having the structure of formula (I) is disclosed:

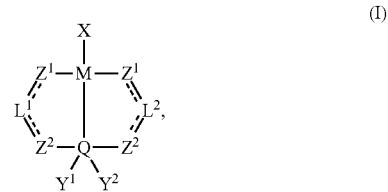

(I)

wherein M is Pt, Pd or Ni; Q is As, Sb or Bi; $Z^1$ is N; $Z^2$ is O or S; $L^1$ and $L^2$ are independently C(O), C—$R^1$ or C—$R^2$; X is a Lewis base; $Y^1$ and $Y^2$ are independently selected from —$OR^3$, —$OR^4$, —$SR^3$ and —$SR^4$, wherein $R^1$ and $R^2$ are independently selected from hydrogen, halogen, cyano, keto, ester, ether, thiol, thioether, thioester, imino, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl, and $C_3$-$C_{15}$ heterocycloalkyl;

wherein $R^3$ and $R^4$ are independently selected from hydrogen, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl, and $C_3$-$C_{15}$ heterocycloalkyl;

wherein the Lewis base can be halogen, N-bonded cyano, nitroso, nitroxyl, N-bonded $C_1$-$C_{10}$ alkyl, $C_1$-$C_{10}$ alkenyl, N-bonded $C_3$-$C_{10}$ cycloalkyl, N-bonded $C_1$-$C_{10}$ heteroalkyl, N-bonded $C_1$-$C_{10}$ heteroalkenyl, N-bonded aryl, N-bonded heteroaryl, N-bonded $C_3$-$C_{15}$ heterocycloalkyl, $NR^5R^6$, N-bonded ligand, S-bonded cyano, sulfonyl, sulfoxyl, thiol, S-bonded thioether, S-bonded thioester, S-bonded $C_1$-$C_{10}$ alkyl, $C_1$-$C_{10}$ alkenyl, S-bonded $C_3$-$C_{10}$ cycloalkyl, S-bonded $C_1$-$C_{10}$ heteroalkyl, S-bonded $C_1$-$C_{10}$ heteroalkenyl, S-bonded aryl, S-bonded heteroaryl, S-bonded $C_3$-$C_{15}$ heterocycloalkyl, —$SR^5$, S-bonded ligand, O-bonded $C_3$-$C_{10}$ cycloalkyl, O-bonded $C_1$-$C_{10}$ heteroalkyl, O-bonded $C_1$-$C_{10}$ heteroalkenyl, O-bonded aryl, O-bonded heteroaryl, O-bonded $C_3$-$C_{15}$ heterocycloalkyl, —$OR^5$, O-bonded carboxylato, O-bonded polycarboxylato, O-bonded ligand, or P-bonded phosphine having formula $P(R^7)_{3-x}(R^8)_x$, where x is 0, 1, 2 or 3;

wherein $R^5$ and $R^6$ are independently selected from hydrogen, O, —$CO_2R^9$, —$COR^9$, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocyclkyl;

wherein $R^7$ and $R^8$ are independently selected from $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl; and wherein $R^9$ is selected from hydrogen, hydroxyl, halogen, amine, thiol, ether, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl.

DETAILED DESCRIPTION

Figure 1A:
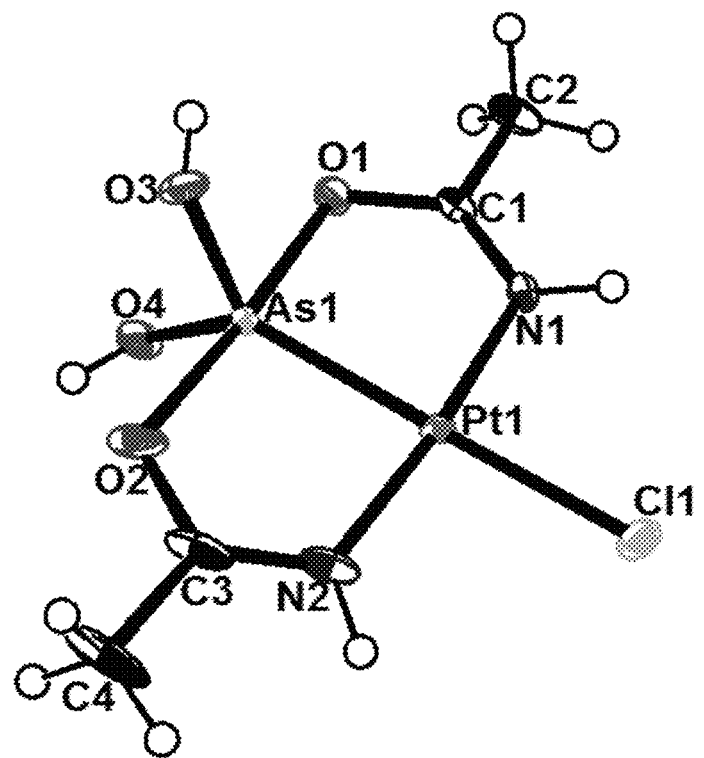
FIG. 1A depicts a thermal ellipsoid plot of compound (1), as crystallized in a triclinic form (solvent molecules omitted for clarity) with space group P-1. The plot is shown at 50% probability level.
Figure 1B:
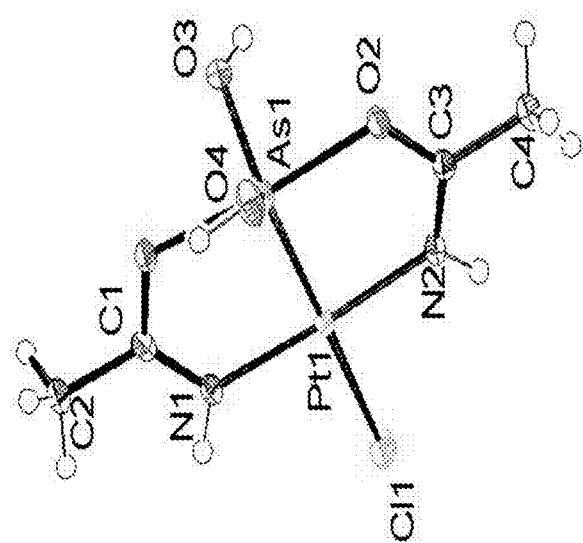
FIG. 1B depicts a thermal ellipsoid plot of compound (1), as crystallized in a monoclinic form with lattice acetamide molecules (solvent molecules omitted for clarity) with space group P2(1)/n. The plot is shown at 50% probability level.
Figure 1B:
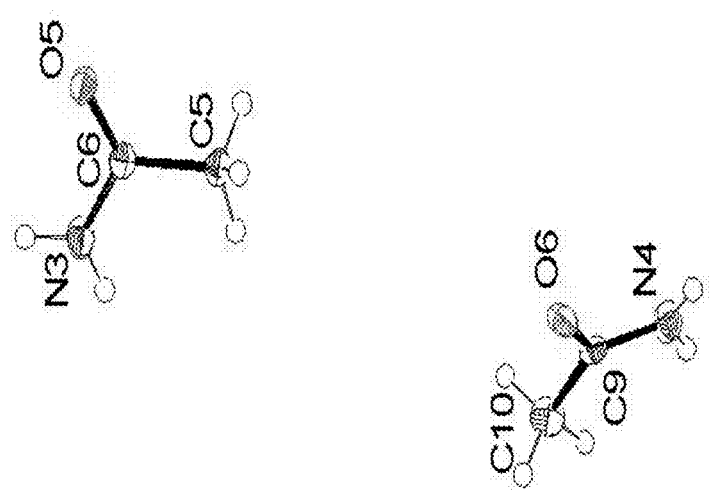
Figure 1C:
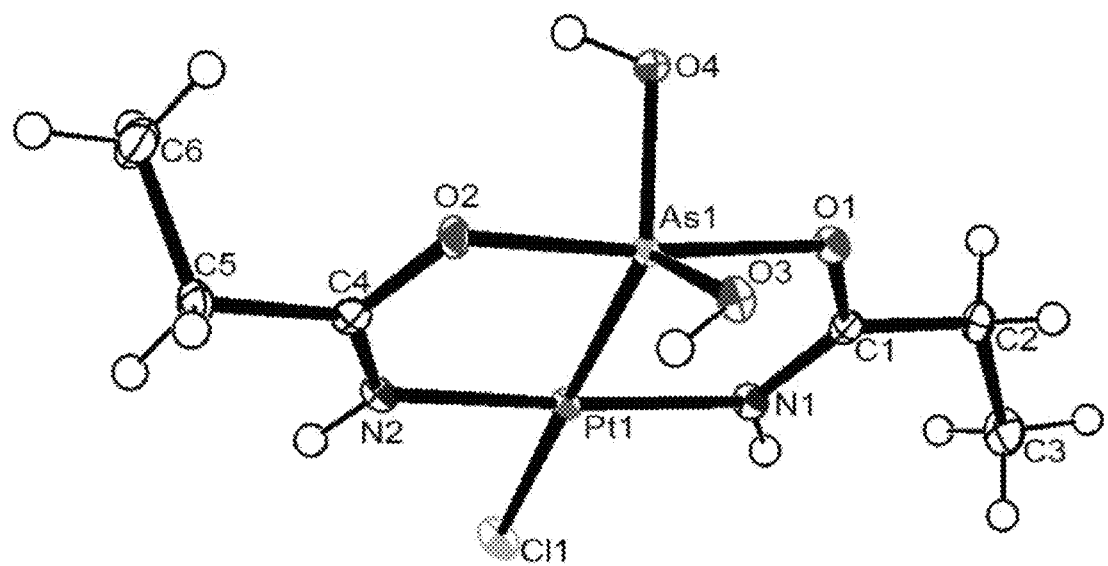
FIG. 1C depicts a thermal ellipsoid plot of compound (2) (solvent molecules omitted for clarity). The plot is shown at 50% probability level.

In the following detailed description, reference is made to the accompanying figures, which form a part hereof. In the figures, similar symbols typically identify similar components, unless context dictates otherwise. Insofar as possible, like parts and modules have the same reference numeral in the figures. The illustrative embodiments described in the detailed description, figures, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

The present disclosure pertains to synthesis and characterization of a novel family of small molecule complexes, such as an aqueous form of $As_2O_3$ bound directly to $Pt^{II}$ as an $As(OH)_2$ moiety, wherein an $As^{III}$ center acts simultaneously as a Lewis acid and a Lewis base. These arsenoplatins and related compounds are surprisingly stable in solution and exhibit unexpected chemical bonding, novel ligand substitution chemistry, and biological activities that are distinct from the parent compounds. The class of arsenoplatins and related compounds demonstrate promising activity as chemotherapeutic agent in drug-resistant cancer cells.

One embodiment pertains to a compound having formula (I):

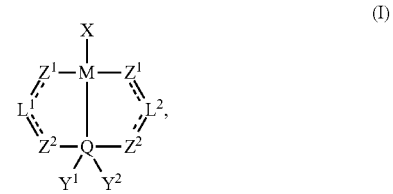

wherein M is Pt, Pd or Ni; Q is As, Sb or Bi; $Z^1$ is N; $Z^2$ is O or S; $L^1$ and $L^2$ are independently C(O), C—$R^1$ or C—$R^2$; X is a Lewis base; $Y^1$ and $Y^2$ are independently selected from —$OR^3$, —$OR^4$, —$SR^3$ and —$SR^4$, wherein $R^1$ and $R^2$ are independently selected from hydrogen, halogen, cyano, keto, ester, ether, thiol, thioether, thioester, imino, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl, and $C_3$-$C_{15}$ heterocycloalkyl;

wherein $R^3$ and $R^4$ are independently selected from hydrogen, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl, and $C_3$-$C_{15}$ heterocycloalkyl;

wherein the Lewis base can be halogen, N-bonded cyano, nitroso, nitroxyl, N-bonded $C_1$-$C_{10}$ alkyl, $C_1$-$C_{10}$ alkenyl, N-bonded $C_3$-$C_{10}$ cycloalkyl, N-bonded $C_1$-$C_{10}$ heteroalkyl, N-bonded $C_1$-$C_{10}$ heteroalkenyl, N-bonded aryl, N-bonded heteroaryl, N-bonded $C_3$-$C_{15}$ heterocycloalkyl, $NR^5R^6$, N-bonded ligand, S-bonded cyano, sulfonyl, sulfoxyl, thiol, S-bonded thioether, S-bonded thioester, S-bonded $C_1$-$C_{10}$ alkyl, $C_1$-$C_{10}$ alkenyl, S-bonded $C_3$-$C_{10}$ cycloalkyl, S-bonded $C_1$-$C_{10}$ heteroalkyl, S-bonded $C_1$-$C_{10}$ heteroalkenyl, S-bonded aryl, S-bonded heteroaryl, S-bonded $C_3$-$C_{15}$ heterocycloalkyl, —$SR^5$, S-bonded ligand, O-bonded $C_3$-$C_{10}$ cycloalkyl, O-bonded $C_1$-$C_{10}$ heteroalkyl, O-bonded $C_1$-$C_{10}$ heteroalkenyl, O-bonded aryl, O-bonded heteroaryl, O-bonded $C_3$-$C_{15}$ heterocycloalkyl, —$OR^5$, O-bonded carboxylato, O-bonded polycarboxylato, O-bonded ligand, or P-bonded phosphine having formula $P(R^7)_{3-x}(R^8)_x$, where x is 0, 1, 2 or 3;

wherein $R^5$ and $R^6$ are independently selected from hydrogen, O, —$CO_2R^9$, —$COR^9$, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl;

wherein $R^7$ and $R^8$ are independently selected from $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl; and wherein $R^9$ is selected from hydrogen, hydroxyl, halogen, amine, thiol, ether, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl.

Another embodiment pertains to a compound having formula (II):

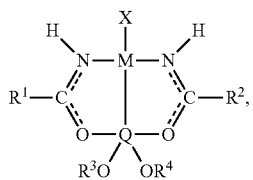

(II)

wherein M is Pt, Pd or Ni; Q is As, Sb or Bi; X is a Lewis base;

wherein $R^1$ and $R^2$ are independently selected from hydrogen, halogen, cyano, keto, ester, ether, thiol, thioether, thioester, imino, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, awl, $C_3$-$C_{15}$ cycloalkyl, heteroaryl, and $C_3$-$C_{15}$ heterocycloalkyl;

wherein $R^3$ and $R^4$ are independently selected from hydrogen, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl and $C_3$-$C_{15}$ heterocycloalkyl;

wherein the Lewis base can be halogen, N-bonded cyano, nitroso, nitroxyl, N-bonded $C_1$-$C_{10}$ alkyl, $C_1$-$C_{10}$ alkenyl, N-bonded $C_3$-$C_{10}$ cycloalkyl, N-bonded $C_1$-$C_{10}$ heteroalkyl, N-bonded $C_1$-$C_{10}$ heteroalkenyl, N-bonded awl, N-bonded heteroaryl, N-bonded $C_3$-$C_{15}$ heterocycloalkyl, $NR^5R^6$, N-bonded ligand, S-bonded cyano, sulfonyl, sulfoxyl, thiol, S-bonded thioether, S-bonded thioester, S-bonded $C_1$-$C_{10}$ alkyl, $C_1$-$C_{10}$ alkenyl, S-bonded $C_3$-$C_{10}$ cycloalkyl, S-bonded $C_1$-$C_{10}$ heteroalkyl, S-bonded $C_1$-$C_{10}$ heteroalkenyl, S-bonded awl, S-bonded heteroaryl, S-bonded $C_3$-$C_{15}$ heterocycloalkyl, —$SR^5$, S-bonded ligand, O-bonded $C_3$-$C_{10}$ cycloalkyl, O-bonded $C_1$-$C_{10}$ heteroalkyl, O-bonded $C_1$-$C_{10}$ heteroalkenyl, O-bonded awl, O-bonded heteroaryl, O-bonded $C_3$-$C_{15}$ heterocycloalkyl, —$OR^5$, O-bonded carboxylato, O-bonded polycarboxylato, O-bonded ligand, or P-bonded phosphine having formula $P(R^7)_{3-x}(R^8)_x$, where x is 0, 1, 2 or 3;

wherein $R^5$ and $R^6$ are independently selected from hydrogen, O, —$CO_2R^9$, —$COR^9$, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl;

wherein $R^7$ and $R^8$ are independently selected from $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl; and wherein $R^9$ is selected from hydrogen, hydroxyl, halogen, amine, thiol, ether, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl.

Another embodiment pertains to a compound having formula (III):

(III)

$$\begin{array}{c} X \\ | \\ Z^1 - Pt - Z^1 \\ L^1 \quad | \quad L^2, \\ Z^2 - As - Z^2 \\ / \quad \backslash \\ HO \quad OH \end{array}$$

wherein $Z^1$ is N; $Z^2$ is O or S; $L^1$ and $L^2$ are independently C(O), C—$R^1$ or C—$R^2$; X is a Lewis base;

wherein $R^1$ and $R^2$ are independently selected from hydrogen, halogen, cyano, keto, ester, ether, thiol, thioether, thioester, imino, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl, and $C_3$-$C_{15}$ heterocycloalkyl;

wherein the Lewis base can be halogen, N-bonded cyano, nitroso, nitroxyl, N-bonded $C_1$-$C_{10}$ alkyl, $C_1$-$C_{10}$ alkenyl, N-bonded $C_3$-$C_{10}$ cycloalkyl, N-bonded $C_1$-$C_{10}$ heteroalkyl, N-bonded $C_1$-$C_{10}$ heteroalkenyl, N-bonded awl, N-bonded heteroaryl, N-bonded $C_3$-$C_{15}$ heterocycloalkyl, $NR^5R^6$, N-bonded ligand, S-bonded cyano, sulfonyl, sulfoxyl, thiol, S-bonded thioether, S-bonded thioester, S-bonded $C_1$-$C_{10}$ alkyl, $C_1$-$C_{10}$ alkenyl, S-bonded $C_3$-$C_{10}$ cycloalkyl, S-bonded $C_1$-$C_{10}$ heteroalkyl, S-bonded $C_1$-$C_{10}$ heteroalkenyl, S-bonded awl, S-bonded heteroaryl, S-bonded $C_3$-$C_{15}$ heterocycloalkyl, —$SR^5$, S-bonded ligand, O-bonded $C_3$-$C_{10}$ cycloalkyl, O-bonded $C_1$-$C_{10}$ heteroalkyl, O-bonded $C_1$-$C_{10}$ heteroalkenyl, O-bonded awl, O-bonded heteroaryl, O-bonded $C_3$-$C_{15}$ heterocycloalkyl, —$OR^5$, O-bonded carboxylato, O-bonded polycarboxylato, O-bonded ligand, or P-bonded phosphine having formula $P(R^7)_{3-x}(R^8)_x$, where x is 0, 1, 2 or 3;

wherein $R^5$ and $R^6$ are independently selected from hydrogen, O, —$CO_2R^9$, —$COR^9$, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl;

wherein $R^7$ and $R^8$ are independently selected from $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl; and wherein $R^9$ is selected from hydrogen, hydroxyl, halogen, amine, thiol, ether, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl.

Another embodiment pertains to a compound having formula (IV):

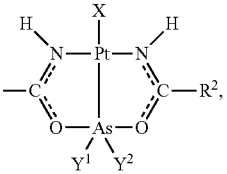

(IV)

wherein X is a Lewis base;
wherein $R^1$ and $R^2$ are independently selected from hydrogen, halogen, cyano, keto, ester, ether, thiol, thioether, thioester, imino, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl, and $C_3$-$C_{15}$ heterocycloalkyl;
wherein $Y^1$ and $Y^2$ are independently selected from —$OR^3$, —$OR^4$, —$SR^3$ and $SR^4$,
wherein $R^3$ and $R^4$ are independently selected from hydrogen, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl, and $C_3$-$C_{15}$ heterocycloalkyl;
wherein the Lewis base can be halogen, N-bonded cyano, nitroso, nitroxyl, N-bonded $C_1$-$C_{10}$ alkyl, $C_1$-$C_{10}$ alkenyl, N-bonded $C_3$-$C_{10}$ cycloalkyl, N-bonded $C_1$-$C_{10}$ heteroalkyl, N-bonded $C_1$-$C_{10}$ heteroalkenyl, N-bonded awl, N-bonded heteroaryl, N-bonded $C_3$-$C_{15}$ heterocycloalkyl, $NR^5R^6$, N-bonded ligand, S-bonded cyano, sulfonyl, sulfoxyl, thiol, S-bonded thioether, S-bonded thioester, S-bonded $C_1$-$C_{10}$ alkyl, $C_1$-$C_{10}$ alkenyl, S-bonded $C_3$-$C_{10}$ cycloalkyl, S-bonded $C_1$-$C_{10}$ heteroalkyl, S-bonded $C_1$-$C_{10}$ heteroalkenyl, S-bonded awl, S-bonded heteroaryl, S-bonded $C_3$-$C_{15}$ heterocycloalkyl, —$SR^5$, S-bonded ligand, O-bonded $C_3$-$C_{10}$ cycloalkyl, O-bonded $C_1$-$C_{10}$ heteroalkyl, O-bonded $C_1$-$C_{10}$ heteroalkenyl, O-bonded awl, O-bonded heteroaryl, O-bonded $C_3$-$C_{15}$ heterocycloalkyl, —$OR^5$, O-bonded carboxylato, O-bonded polycarboxylato, O-bonded ligand, or P-bonded phosphine having formula $P(R^7)_{3-x}(R^8)_x$, where x is 0, 1, 2 or 3;
wherein $R^5$ and $R^6$ are independently selected from hydrogen, O, —$CO_2R^9$, —$COR^9$, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl;
wherein $R^7$ and $R^8$ are independently selected from $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl; and
wherein $R^9$ is selected from hydrogen, hydroxyl, halogen, amine, thiol, ether, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl.

Another embodiment pertains to a compound having formula (V):

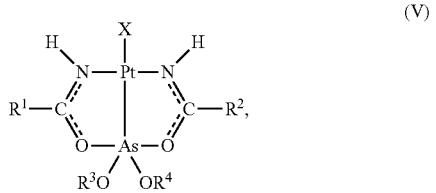

(V)

wherein X is a Lewis base;
wherein $R^1$ and $R^2$ are independently selected from hydrogen, halogen, cyano, keto, ester, ether, thiol, thioether, thioester, imino, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl, and $C_3$-$C_{15}$ heterocycloalkyl;
wherein $R^3$ and $R^4$ are independently selected from hydrogen, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl, and $C_3$-$C_{15}$ heterocycloalkyl;
wherein the Lewis base can be halogen, N-bonded cyano, nitroso, nitroxyl, N-bonded $C_1$-$C_{10}$ alkyl, $C_1$-$C_{10}$ alkenyl, N-bonded $C_3$-$C_{10}$ cycloalkyl, N-bonded $C_1$-$C_{10}$ heteroalkyl, N-bonded $C_1$-$C_{10}$ heteroalkenyl, N-bonded awl, N-bonded heteroaryl, N-bonded $C_3$-$C_{15}$ heterocycloalkyl, $NR^5R^6$, N-bonded ligand, S-bonded cyano, sulfonyl, sulfoxyl, thiol, S-bonded thioether, S-bonded thioester, S-bonded $C_1$-$C_{10}$ alkyl, $C_1$-$C_{10}$ alkenyl, S-bonded $C_3$-$C_{10}$ cycloalkyl, S-bonded $C_1$-$C_{10}$ heteroalkyl, S-bonded $C_1$-$C_{10}$ heteroalkenyl, S-bonded awl, S-bonded heteroaryl, S-bonded $C_3$-$C_{15}$ heterocycloalkyl, —$SR^5$, S-bonded ligand, O-bonded $C_3$-$C_{10}$ cycloalkyl, O-bonded $C_1$-$C_{10}$ heteroalkyl, O-bonded $C_1$-$C_{10}$ heteroalkenyl, O-bonded awl, O-bonded heteroaryl, O-bonded $C_3$-$C_{15}$ heterocycloalkyl, —$OR^5$, O-bonded carboxylato, O-bonded polycarboxylato, O-bonded ligand, or P-bonded phosphine having formula $P(R^7)_{3-x}(R^8)_x$, where x is 0, 1, 2 or 3;
wherein $R^5$ and $R^6$ are independently selected from hydrogen, O, —$CO_2R^9$, —$COR^9$, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl;
wherein $R^7$ and $R^8$ are independently selected from $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl; and
wherein $R^9$ is selected from hydrogen, hydroxyl, halogen, amine, thiol, ether, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl.

Another embodiment pertains to a compound having formula (VI):

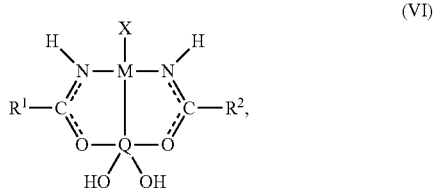

(VI)

wherein M is Pt, Pd or Ni; Q is As, Sb or Bi; X is a Lewis base;
wherein $R^1$ and $R^2$ are independently selected from hydrogen, halogen, cyano, keto, ester, ether, thiol, thioether, thioester, imino, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl, and $C_3$-$C_{15}$ heterocycloalkyl; and
wherein the Lewis base can be halogen, N-bonded cyano, nitroso, nitroxyl, N-bonded $C_1$-$C_{10}$ alkyl, $C_1$-$C_{10}$ alkenyl, N-bonded $C_3$-$C_{10}$ cycloalkyl, N-bonded $C_1$-$C_{10}$ heteroalkyl, N-bonded $C_1$-$C_{10}$ heteroalkenyl, N-bonded awl, N-bonded heteroaryl, N-bonded $C_3$-$C_{15}$ heterocycloalkyl, $NR^5R^6$, N-bonded ligand, S-bonded cyano, sulfonyl, sulfoxyl, thiol, S-bonded thioether, S-bonded thioester, S-bonded $C_1$-$C_{10}$ alkyl, $C_1$-$C_{10}$ alkenyl, S-bonded $C_3$-$C_{10}$ cycloalkyl, S-bonded $C_1$-$C_{10}$ heteroalkyl, S-bonded $C_1$-$C_{10}$ heteroalkenyl, S-bonded awl, S-bonded heteroaryl, S-bonded $C_3$-$C_{15}$ heterocycloalkyl, —$SR^5$, S-bonded ligand, O-bonded $C_3$-$C_{10}$ cycloalkyl, O-bonded $C_1$-$C_{10}$ heteroalkyl, O-bonded $C_1$-$C_{10}$ heteroalkenyl, O-bonded awl, O-bonded heteroaryl, O-bonded $C_3$-$C_{15}$ heterocycloalkyl, —$OR^5$, O-bonded carboxylato, O-bonded polycarboxylato, O-bonded ligand, or P-bonded phosphine having formula $P(R^7)_{3-x}(R^8)_x$, where x is 0, 1, 2 or 3;

wherein R⁵ and R⁶ are independently selected from hydrogen, O, —CO₂R⁹, —COR⁹, C₁-C₁₀ alkyl, C₁-C₁₀ alkenyl, awl, heteroaryl, C₃-C₁₅ cycloalkyl and C₃-C₁₅ heterocycloalkyl;
wherein R⁷ and R⁸ are independently selected from C₁-C₁₀ alkyl, C₁-C₁₀ alkenyl, aryl, heteroaryl, C₃-C₁₅ cycloalkyl and C₃-C₁₅ heterocycloalkyl; and
wherein R⁹ is selected from hydrogen, hydroxyl, halogen, amine, thiol, ether, C₁-C₁₀ alkyl, C₁-C₁₀ alkenyl, aryl, heteroaryl, C₃-C₁₅ cycloalkyl and C₃-C₁₅ heterocycloalkyl.

Another embodiment pertains to a compound having formula (VII):

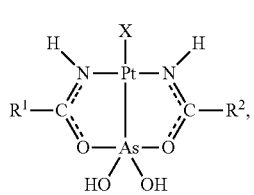

(VII)

wherein X is a Lewis base;
wherein R¹ and R² are independently selected from hydrogen, halogen, cyano, keto, ester, ether, thiol, thioester, imino, C₁-C₁₀ alkyl, C₁-C₁₀ alkenyl, alkynyl, alkoxyl, amino, amidyl, immino, sulfonyl, sulfoxyl, phosphoryl, phosphoryl ester, glycosyl, aryl, C₃-C₁₅ cycloalkyl, heteroaryl, and C₃-C₁₅ heterocycloalkyl; and
wherein the Lewis base can be halogen, N-bonded cyano, nitroso, nitroxyl, N-bonded C₁-C₁₀ alkyl, C₁-C₁₀ alkenyl, N-bonded C₃-C₁₀ cycloalkyl, N-bonded C₁-C₁₀ heteroalkyl, N-bonded C₁-C₁₀ heteroalkenyl, N-bonded aryl, N-bonded heteroaryl, N-bonded C₃-C₁₅ heterocycloalkyl, NR⁵R⁶, N-bonded ligand, S-bonded cyano, sulfonyl, sulfoxyl, thiol, S-bonded thioether, S-bonded thioester, S-bonded C₁-C₁₀ alkyl, C₁-C₁₀ alkenyl, S-bonded C₃-C₁₀ cycloalkyl, S-bonded C₁-C₁₀ heteroalkyl, S-bonded C₁-C₁₀ heteroalkenyl, S-bonded aryl, S-bonded heteroaryl, S-bonded C₃-C₁₅ heterocycloalkyl, —SR⁵, S-bonded ligand, O-bonded C₃-C₁₀ cycloalkyl, O-bonded C₁-C₁₀ heteroalkyl, O-bonded C₁-C₁₀ heteroalkenyl, O-bonded awl, O-bonded heteroaryl, O-bonded C₃-C₁₅ heterocycloalkyl, —OR⁵, O-bonded carboxylato, O-bonded polycarboxylato, O-bonded ligand, or P-bonded phosphine having formula P(R⁷)₃₋ₓ(R⁸)ₓ, where x is 0, 1, 2 or 3;
wherein R⁵ and R⁶ are independently selected from hydrogen, O, —CO₂R⁹, —COR⁹, C₁-C₁₀ alkyl, C₁-C₁₀ alkenyl, aryl, heteroaryl, C₃-C₁₅ cycloalkyl and C₃-C₁₅ heterocycloalkyl;
wherein R⁷ and R⁸ are independently selected from C₁-C₁₀ alkyl, C₁-C₁₀ alkenyl, aryl, heteroaryl, C₃-C₁₅ cycloalkyl and C₃-C₁₅ heterocycloalkyl; and
wherein R⁹ is selected from hydrogen, hydroxyl, halogen, amine, thiol, ether, C₁-C₁₀ alkyl, C₁-C₁₀ alkenyl, aryl, heteroaryl, C₃-C₁₅ cycloalkyl and C₃-C₁₅ heterocycloalkyl.

In the cited exemplary embodiments, the alkyl- and cycloalkyl-containing substituents can be branched or unbranched, substituted or unsubstituted, saturated or unsaturated, including combinations of different extents of substitution, branching and saturation. Likewise, the alkenyl-containing substituents can be branched or unbranched, substituted or unsubstituted, different extents of unsaturation, including combinations of different extents of substitution, branching and saturation. Furthermore, the cited aryl substituents include substituted and unsubstituted aryl moieties. Likewise, the cited heteroaryl and heterocycloalkyl substituents include at least one heteroatom different from carbon (C) as part of the ring system, such as nitrogen (N), oxygen (O), sulfur (S), phosphorous (P) or boron (B). Where substituents include lone electron pairs available for bonding to other atoms, those substituents can include further substitutions. Examples of moieties that can include further substitutions include keto, ester, ether, thioether, thioester, imino, amino, amidyl, immino, sulfonyl, sulfoxyl, phosphoryl, phosphoryl ester, glycosyl and the like. Exemplary halogen substituents include —F, —Cl, —Br and —I.

As used herein, "N-bonded" refers to a lone pair of electrons from nitrogen being coordinated to M, where M is Pt, Pd or Ni. Where "N-bonded" modifies "alkyl" or "aryl," the M-coordinating nitrogen forms a bond to the respective alkyl or aryl, wherein M is Pt, Pd or Ni. An exemplary "N-bonded alkyl" moiety is a methylamine radical. An exemplary "N-bonded aryl" moiety is an aniline radical. Where "N-bonded" modifies a heteroatom-containing substituent, such as "heterocycloalkyl" or "heteroaryl," the M-coordinating nitrogen forms part of the ring system of the respective heterocycloalkyl or heteroaryl, wherein M is Pt, Pd or Ni. An exemplary "N-bonded heterocycloalkyl" is a morpholine radical. An exemplary "N-bonded heteroaryl" is a pyridine radical. As used herein, "N-bonded ligand" refers to an M-coordinating nitrogen forming a bond to a ligand, wherein M is Pt, Pd or Ni and ligand includes an amino acid, a peptide, a protein, a glycan, a peptidoglycan, a polysaccharide, a biologically-compatible polymer (for example, a polyethylene glycol (PEG) polymer) or an oligonucleotide.

As used herein, "S-bonded" refers to a lone pair of electrons from sulfur being coordinated to M, where M is Pt, Pd or Ni. Where "S-bonded" modifies "alkyl" or "awl," the M-coordinating sulfur forms a bond to the respective alkyl or aryl, wherein M is Pt, Pd or Ni. An exemplary "S-bonded alkyl" moiety is a methanethiol radical. An exemplary "S-bonded aryl" moiety is a thiophenol radical. Where "S-bonded" modifies a heteroatom-containing substituent, such as "heterocycloalkyl" or "heteroaryl," the M-coordinating sulfur forms part of the ring system of the respective heterocycloalkyl or heteroaryl, wherein M is Pt, Pd or Ni. An exemplary "S-bonded heterocycloalkyl" is a thioxane radical. An exemplary "S-bonded heteroaryl" is a thiophene radical. As used herein, "S-bonded ligand" refers to an M-coordinating sulfur forming a bond to a ligand, wherein M is Pt, Pd or Ni and ligand includes an amino acid, a peptide, a protein, a glycan, a peptidoglycan, a polysaccharide, or an oligonucleotide.

As used herein, "O-bonded" refers to a lone pair of electrons from oxygen being coordinated to M, where M is Pt, Pd or Ni. Where "O-bonded" modifies "alkyl" or "aryl," the M-coordinating oxygen forms a bond to the respective alkyl or aryl, wherein M is Pt, Pd or Ni. An exemplary "O-bonded alkyl" moiety is a methoxy radical. An exemplary "O-bonded aryl" moiety is a phenol radical. Where "O-bonded" modifies a heteroatom-containing substituent, such as "heterocycloalkyl" or "heteroaryl," the M-coordinating oxygen forms part of the ring system of the respective heterocycloalkyl or heteroaryl, wherein M is Pt, Pd or Ni. An exemplary "O-bonded heterocycloalkyl" is a tetrahydropyran radical. An exemplary "O-bonded heteroaryl" is a furan radical. As used herein, "O-bonded ligand" refers to an M-coordinating oxygen forming a bond to a ligand, wherein M is Pt, Pd or Ni and ligand includes an amino acid, a peptide, a protein, a glycan, a peptidoglycan, a polysaccharide, or an oligonucleotide.

As used herein, "P-bonded" refers to a lone pair of electrons from phosphorous being coordinated to M, where M is Pt, Pd or Ni. Where "P-bonded" modifies "phosphine," the M-coordinating phosphorous (P) is the phosphorous in the formula $P(R^7)_{3-x}(R^8)_x$, where x is 0, 1, 2 or 3 and wherein M is Pt, Pd or Ni.

An "amino acid" refers to any monomer unit that can be incorporated into a peptide, polypeptide, or protein. As used herein, the term "amino acid" includes the following twenty natural or genetically encoded alpha-amino acids: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). In cases where "X" residues are undefined, these should be defined as "any amino acid." The structures of these twenty natural amino acids are shown in, e.g., Stryer et al., Biochemistry, 5.sup.th ed., Freeman and Company (2002), which is incorporated by reference. Additional amino acids, such as selenocysteine and pyrrolysine, can also be genetically coded for (Stadtman (1996) "Selenocysteine," Annu Rev Biochem. 65:83-100 and Ibba et al. (2002) "Genetic code: introducing pyrrolysine," Curr Biol. 12(13): R464-R466, which are both incorporated by reference). The term "amino acid" also includes unnatural amino acids, modified amino acids (e.g., having modified side chains and/or backbones), and amino acid analogs. See, e.g., Zhang et al. (2004) "Selective incorporation of 5-hydroxytryptophan into proteins in mammalian cells," Proc. Natl. Acad. Sci. U.S.A. 101(24):8882-8887, Anderson et al. (2004) "An expanded genetic code with a functional quadruplet codon" Proc. Natl. Acad. Sci. U.S.A. 101(20):7566-7571, Ikeda et al. (2003) "Synthesis of a novel histidine analogue and its efficient incorporation into a protein in vivo," Protein Eng. Des. Sel. 16(9):699-706, Chin et al. (2003) "An Expanded Eukaryotic Genetic Code," Science 301(5635):964-967, James et al. (2001) "Kinetic characterization of ribonuclease S mutants containing photoisomerizable phenylazophenylalanine residues," Protein Eng. Des. Sel. 14(12):983-991, Kohrer et al. (2001) "Import of amber and ochre suppressor tRNAs into mammalian cells: A general approach to site-specific insertion of amino acid analogues into proteins," Proc. Natl. Acad. Sci. U.S.A. 98(25):14310-14315, Bacher et al. (2001) "Selection and Characterization of *Escherichia coli* Variants Capable of Growth on an Otherwise Toxic Tryptophan Analogue," J. Bacteriol. 183(18):5414-5425, Hamano-Takaku et al. (2000) "A Mutant *Escherichia coli* Tyrosyl-tRNA Synthetase Utilizes the Unnatural Amino Acid Azatyrosine More Efficiently than Tyrosine," J. Biol. Chem. 275(51):40324-40328, and Budisa et al. (2001) "Proteins with {beta}-(thienopyrrolypalanines as alternative chromophores and pharmaceutically active amino acids," Protein Sci. 10(7):1281-1292, which are each incorporated by reference.

To further illustrate, an amino acid is typically an organic acid that includes a substituted or unsubstituted amino group, a substituted or unsubstituted carboxy group, and one or more side chains or groups, or analogs of any of these groups. Exemplary side chains include, e.g., thiol, seleno, sulfonyl, alkyl, aryl, acyl, keto, azido, hydroxyl, hydrazine, cyano, halo, hydrazide, alkenyl, alkynl, ether, borate, boronate, phospho, phosphono, phosphine, heterocyclic, enone, imine, aldehyde, ester, thioacid, hydroxylamine, or any combination of these groups. Other representative amino acids include, but are not limited to, amino acids comprising photoactivatable cross-linkers, metal binding amino acids, spin-labeled amino acids, fluorescent amino acids, metal-containing amino acids, amino acids with novel functional groups, amino acids that covalently or noncovalently interact with other molecules, photocaged and/or photoisomerizable amino acids, radioactive amino acids, amino acids comprising biotin or a biotin analog, glycosylated amino acids, other carbohydrate modified amino acids, amino acids comprising polyethylene glycol or polyether, heavy atom substituted amino acids, chemically cleavable and/or photocleavable amino acids, carbon-linked sugar-containing amino acids, redox-active amino acids, amino thioacid containing amino acids, and amino acids comprising one or more toxic moieties.

The term "peptide" refers to a synthetic or naturally occurring polymer of amino acids having two or more amino acid moieties joined together through amide bonds. Example of peptides include glutathione, Substance P, calcitonin, Enkephalin, and B-type Natrinuretic Peptide. The term "protein" refers to a synthetic or naturally occurring polymer that is typically encoded by a gene. Naturally occurring peptides are typically derived from proteins by post-translational processing. For the purposes of this disclosure, peptides and proteins together form the group termed "polypeptides," which encompasses all polymers composed of only amino acids.

An oligonucleotide, as used herein, refers to a polynucleotide having two or more nucleobases connected together through phosphoribosyl bonds, phosphodioxyribosyl bonds, peptidyldeoxyribosyl bounds, peptidyldeoxyribosyl bonds, phosphorothiolate containing linkages, among others. Oligonucleotide includes RNA polymers, DNA polymers, RNA-DNA mixed polymers, peptide nucleic acid polymers, locked nucleic acids polymers and mixtures of the foregoing polymers. Oligonucleotides can include modified bases, modified internucleotidyl groups (for example, modified ribose or deoxyribose moieties and/or modified phosphate, phosphorothiolate, or peptide moieties) and/or modified 5' and 3' terminal groups (for example, a blocking 3'-C3 spacer group).

Exemplary embodiments of formulas (I)-(VII) include compounds (1)-(19) as illustrated below.

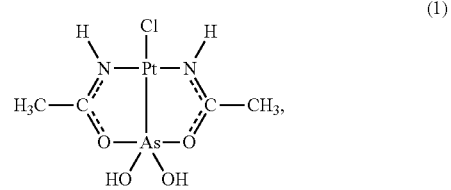

(1)

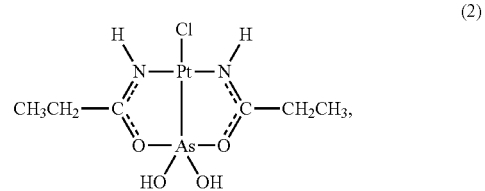

(2)

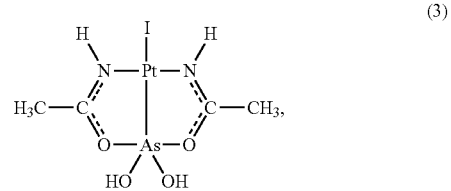

(3)

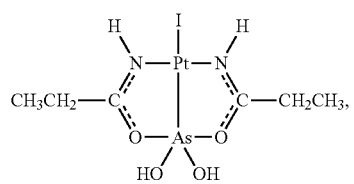
(4)
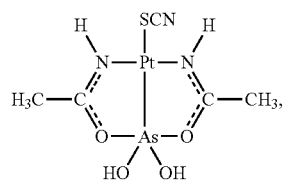
(5)
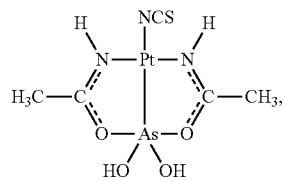
(6)
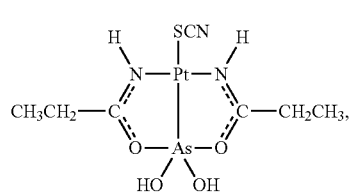
(7)
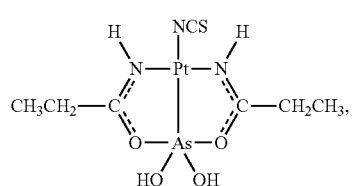
(8)
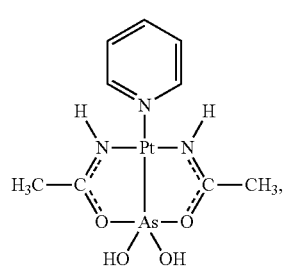
(9)
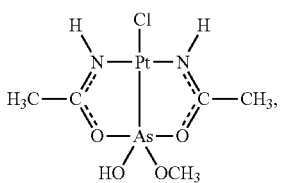
(10)
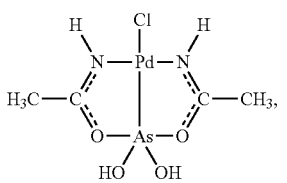
(11)
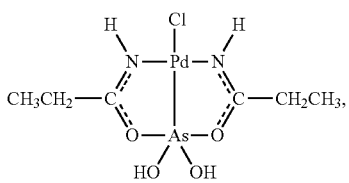
(12)
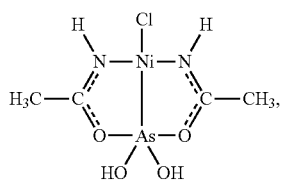
(13)
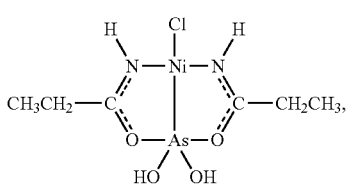
(14)
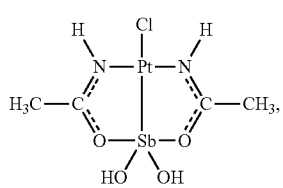
(15)
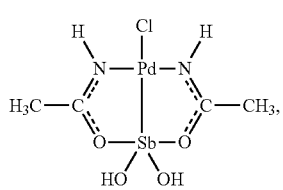
(16)
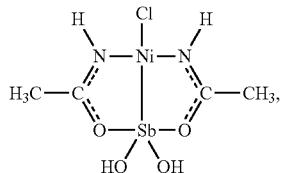
(17)
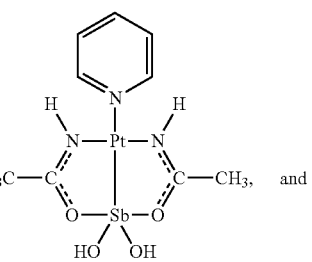
(18)
and -continued (19)

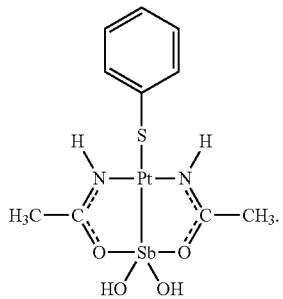

The synthesis of the disclosed compounds can be accomplished with minor modifications of the following synthetic procedures. One procedure pertains to an unexpected synthesis outcome that uses relatively prolonged, high temperature conditions than normally done to prepare liganded M-Q coordination complexes, wherein M is Pt, Pd or Ni and Q is As, Sb or Bi. Typically, such liganded M-Q coordination complexes are synthesized under mild temperature conditions, such as ambient or slightly supra-ambient temperature conditions (~15° C. to ~37° C.) to preserve the oxidation state of the M of the M-Q coordination complexes. Unusually, the some of the M-Q coordination complexes could only be achieved following incubation at 90° C. for ~72 hours. For example, compound (1) can be synthesized by heating cisplatin with $As_2O_3$ in an acetonitrile-water mixture (9:1, v/v) at 90° C. for three days. However, the yield of compound (1) increases from 23% to 75% when the starting material is $K_2[PtCl_4]$.

Alternative, milder synthetic procedures were discovered that enabled other species of the disclosed compounds to be obtained. Exemplary syntheses of the disclosed compounds are provided herein. For example, the preparation of compounds of formula (II) include the method according to scheme (1).

(scheme 1)

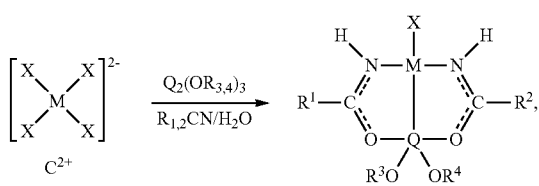

wherein "$Q_2(OR_{3,4})_3$" represents a mixture of $Q_2(OR_3)_3$ and $Q_2(OR_4)_3$ and "$R_{1,2}CN$" represents a mixture of $R_1CN$ and $R_2CN$ and "$C^{2+}$" represents either two monovalent cations or a single divalent cation.

The preparation of compounds of formula (VI) include the method according to scheme (2).

(scheme 2)

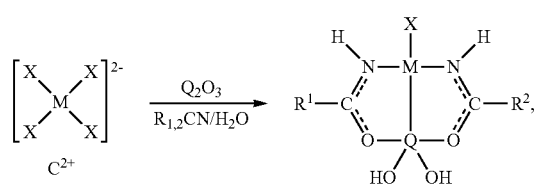

wherein "$R_{1,2}CN$" represents a mixture of $R_1CN$ and $R_2CN$ and "$C^{2+}$" represents either two monovalent cations or a single divalent cation.

The preparation of compounds of formula (VII) include the method according to scheme (3).

(scheme 3)

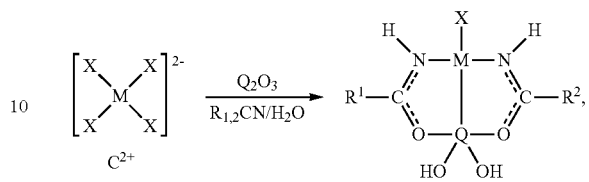

wherein "$R_{1,2}CN$" represents a mixture of $R_1CN$ and $R_2CN$ and "$C^{2+}$" represents either two monovalent cations or a single divalent cation.

The preparation of compounds of formulas (I)-(VII), wherein the X substituent is replaced with a different X substituent can be done in several ways. In one embodiment, wherein the X substituent contains both an moiety having N-bonded and S-bonded potential, the alternative X substituent can be obtained by thermal isomerization, as depicted in scheme (4) for S-bonded SCN conversion to N-bonded NCS.

(scheme 4)

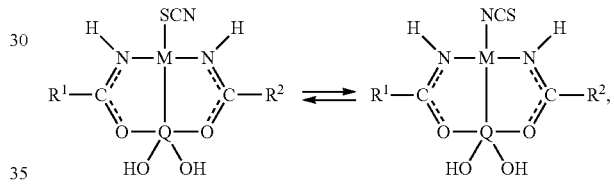

wherein "$R_{1,2}CN$" represents a mixture of $R_1CN$ and $R_2CN$ and "$C^{2+}$" represents either two monovalent cations or a single divalent cation.

In another embodiment, the replacement of X substituents can be achieved by an exchange reaction, wherein one X substituent, such as a halogen can be replaced by an non-halogen substituent, such as an X substituent having an N-bonded group or an S-bonded group according to the schemes (5) and (6).

(scheme 5)

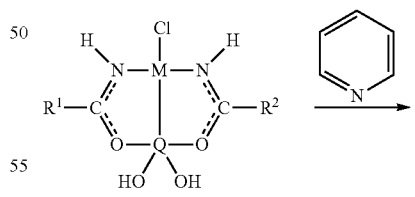

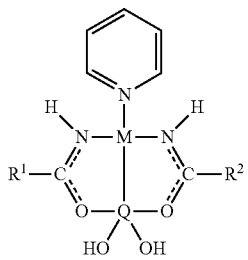

(scheme 6)

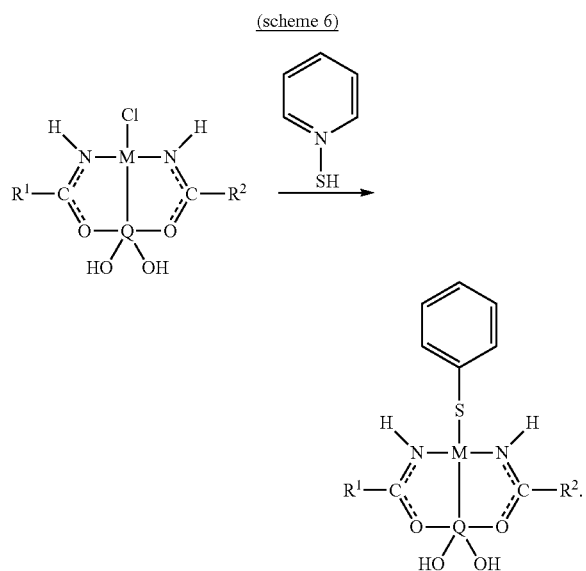

For example variations on formula (VII) (exemplary species: compound (1)) are accessible by varying substituent on the nitrile. For instance, compound (2) can be obtained from the reaction of $K_2[PtCl_4]$ with $As_2O_3$ in the presence of propionitrile. Conditions for synthesis of compound (2) were different from compound (1) because of the different miscibility of propionitrile in water (1:9, v/v). Compound (2) is obtained at mom temperature after 4 days, whereas compound (1) is obtained at elevated temperatures.

In compounds (1) and (2), the Pt(11) center adopts a square planar geometry, with arsenic, chloride, and two nitrogen donors in a trans configuration. The nitrogen donors are derived from acetamide (propanamide) formed via Pt-assisted acetonitrile (propionitrile) hydrolysis in situ. The Pt—N bond lengths in 1a (Pt1-N1=2.000(3) Å and Pt1-N2=2.004(3) Å are consistent with the Pt—N bond lengths obtained in other Pt(II) complexes with the deprotonated form of acetamide, Pt—N=2.004(11) and Pt—N=2.000(3) Å. Similar bond lengths are obtained in compound (1b) [crystal form b] and compound (2) (see Example 21). The N1-C1 and O1-C1 bond lengths (both 1.302(4) Å) and N2-C3 and O2-C3 (1.289(6) and 1.297(6) Å) in 1a are indicative of a high degree of delocalization present in the chelate rings formed by bridging N, O acetamido ligands (Example 21).

The M-Q core is also stable to ligand substitution reactions. In general, for example, hydrolysis of Pt—Cl bonds is slow ($t_{1/2}$=2 h at 37° C. and 4 mM Cl$^-$) and rapid substitution usually requires addition of reagents such as $AgNO_3$. The substitution of the Cl$^-$ ligand in compound (1) with SCN$^-$ in water occurs immediately at room temperature to provide compound (5) and is likely driven by the trans effect of the arsenic moiety.

Figure 1D:
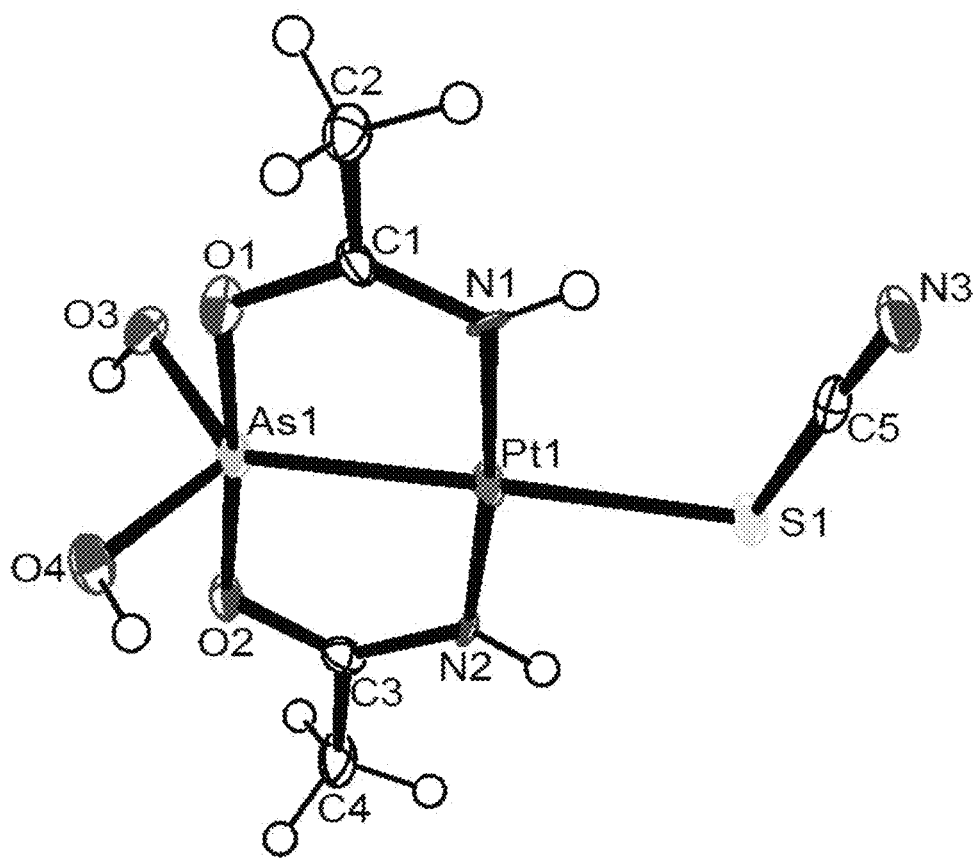
FIG. 1D depicts a thermal ellipsoid plot of compound (5) (solvent molecules omitted for clarity). The plot is shown at 50% probability level.
Figure 2:
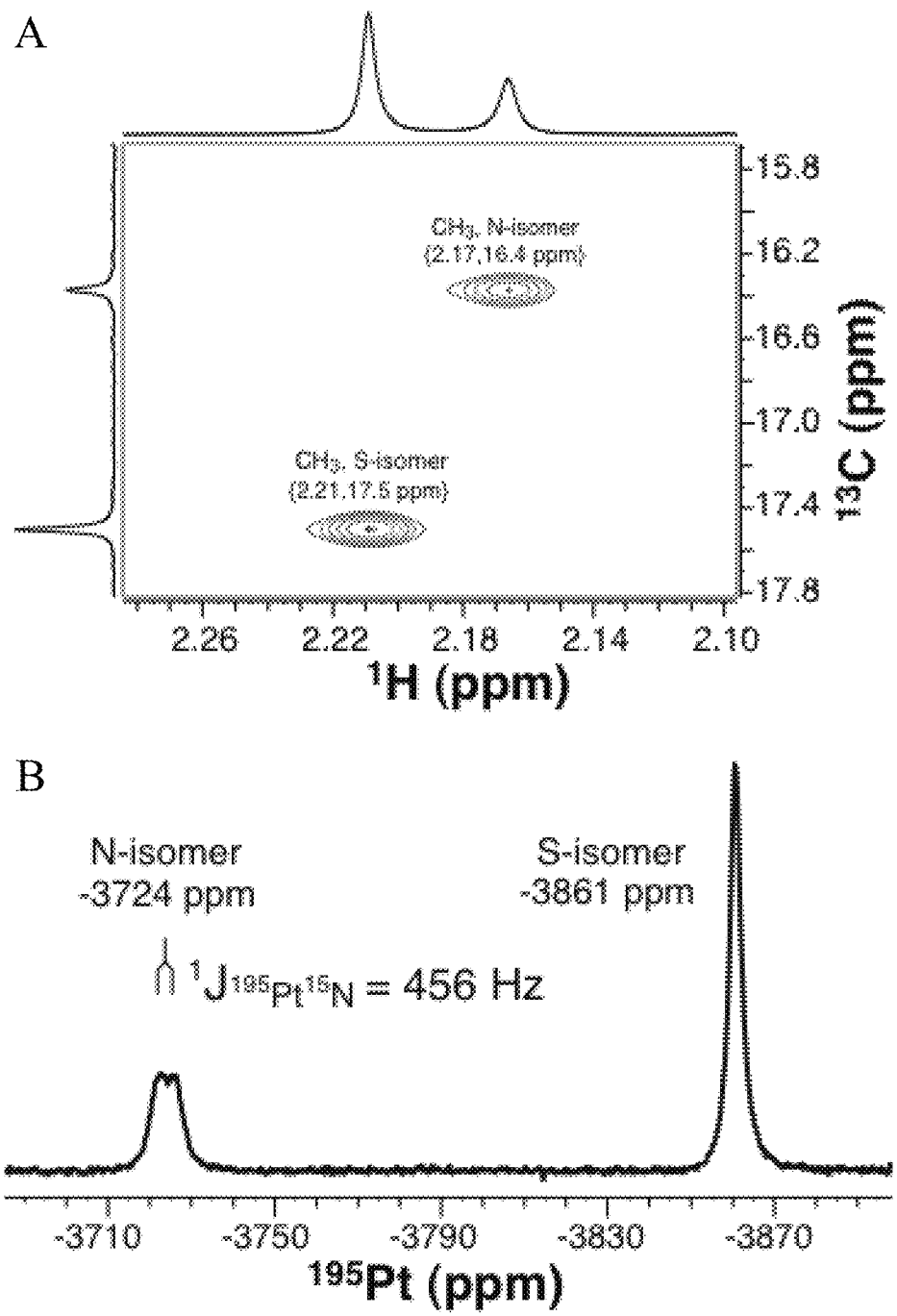
FIG. 2A depicts a $^1H$-$^{13}C$ HSQC NMR spectrum of compound (5) (with $S^{13}C^{15}N$) in [$D_6$]DMSO, acquired at 25° C. at 600 MHz $^1H$ with high resolution in the indirect ($^{13}C$) dimension to distinguish the methyl resonances of the N- and S-isomers.
FIG. 2B depicts a $^{195}Pt$ NMR spectrum of compound (5) (with $S^{13}C^{15}N$) in [$D_6$]DMSO, referenced indirectly to $^1H$ TMS such that $Na_2^{195}PtCl_6$ resonates at 0.0 ppm. The 456 Hz splitting of the $^{195}Pt$ peak at −3724 ppm arises from scalar coupling to the $SC^{15}N$.

Solution NMR and X-ray crystallography confirm that the Pt—As bond remained intact. Crystals suitable for a single crystal X-ray analysis were obtained when compound (5) was synthesized in a 1:1 water/methanol mixture, where the SCN ion is bound to Pt(II) through the sulfur atom (FIG. 1D). NMR spectroscopy reveals facile linkage isomerization of compound (5) in solution at mom temperature. Specifically, upon dissolving compound (5) in [$D_6$]DMSO solution equilibrium mixture of 64±1.2% of S-isomer (compound (5)) and 36%±1.5 of N-isomer (compound (6)) is quickly established, i.e., the $^1$H NMR spectrum obtained after 5 min upon dissolution of compound (5) does not change over time. Assignments of chemical shifts for the S- and N-bound isomers signals are based on multidimensional $^{195}$Pt and $^{15}$N NMR spectroscopy on sample of compound (5) which is synthesized using thiocyanate enriched in $^{13}$C and $^{15}$N at 99% (FIG. 2).

Initial formation of compound (5) with S-bound thiocyanate can be kinetically or thermodynamically controlled, but both isomers (that is, compounds (5) and (6)) are sufficiently stable in [$D_6$]DMSO solution to be observed using NMR spectroscopy. The N-isomer of compound (5) is enthalpically favored in solution by 15.7 kJmol$^{-1}$. Interestingly, only the S-linked complex of compound (5) could be isolated in the solid state, which may be the result of both rapid equilibration and a lower solubility for the S-isomer.

Biological Activity of Disclosed Compounds as Anticancer Agents

Compounds (1) and (2) demonstrate significant anticancer activity in a panel of human cancer cell lines (FIG. 3 and Example 22) and also overcomes one of the most significant limitations of platinum drugs, namely tumor-based drug resistance mechanisms. The ovarian cisplatin resistant A2780$^{CP}$ cancer cell line is of special interest since it encompasses all of the known major mechanisms of resistance to cisplatin (reduced uptake, increased level of glutathione, increased DNA repair, and tolerance to Pt(II)-induced lesions). The results show that compound (1) exhibited more than twice the cytotoxicity of cisplatin against the cisplatin resistant cell line A2780$^{CP}$ ($IC_{50}$ 21.4±1.8 µM versus 47.3±2.1 µM) (See FIG. 3 and Example 22, Table 8). The ability of compound (1) to circumvent cisplatin-acquired resistance was determined from the resistance factor (RF), and an RF value of <2 denotes no cross-resistance. In the case of ovarian A2780 and A2780$^{CP}$ cell lines all approved platinum drugs have RFs between 6.1 and 16.0. The RF of 1.1 for compound (1) indicates that it is far more effective at killing this cisplatin resistant cancer cell line and may be able to bypass drug resistance mechanism(s) that lower cisplatin cytotoxicity.

Figure 3:
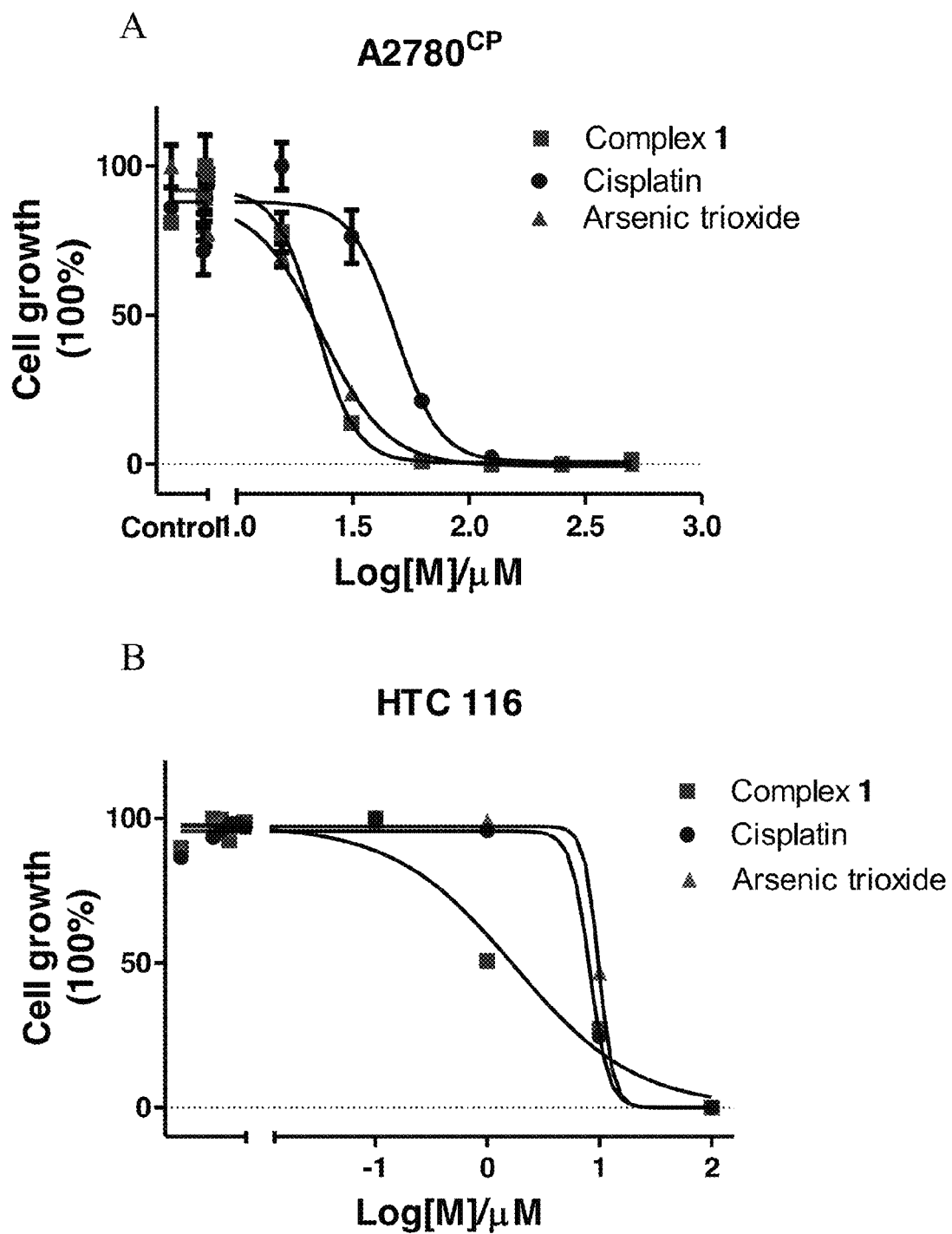
FIG. 3A depicts a dose response curve for cell growth inhibition of ovarian cisplatin-resistant cells $A2780^{CP}$ following exposure to one of compound (1), cisplatin or $As_2O_3$.
FIG. 3B depicts a dose response curve for cell growth inhibition of colon HCT-116 cells following exposure to one of compound (1), cisplatin or $As_2O_3$.
FIG. 3C depicts a dose response curve for cell growth inhibition of glioblastoma U-87 cells following exposure to one of compound (1), cisplatin or $As_2O_3$.
FIG. 3D depicts a dose response curve for cell growth inhibition of ovarian cisplatin-sensitive cells A2780 cells following exposure to one of compound (1), cisplatin or $As_2O_3$.
FIG. 3E depicts a dose response curve for cell growth inhibition of triple-negative breast MDA-MB-231 cells following exposure to one of compound (1), cisplatin or $As_2O_3$.
FIG. 3F depicts a dose response curve for cell growth inhibition of multiple myeloma RPMI 8226 cells following exposure to one of compound (1), cisplatin or $As_2O_3$.
Figure 3:
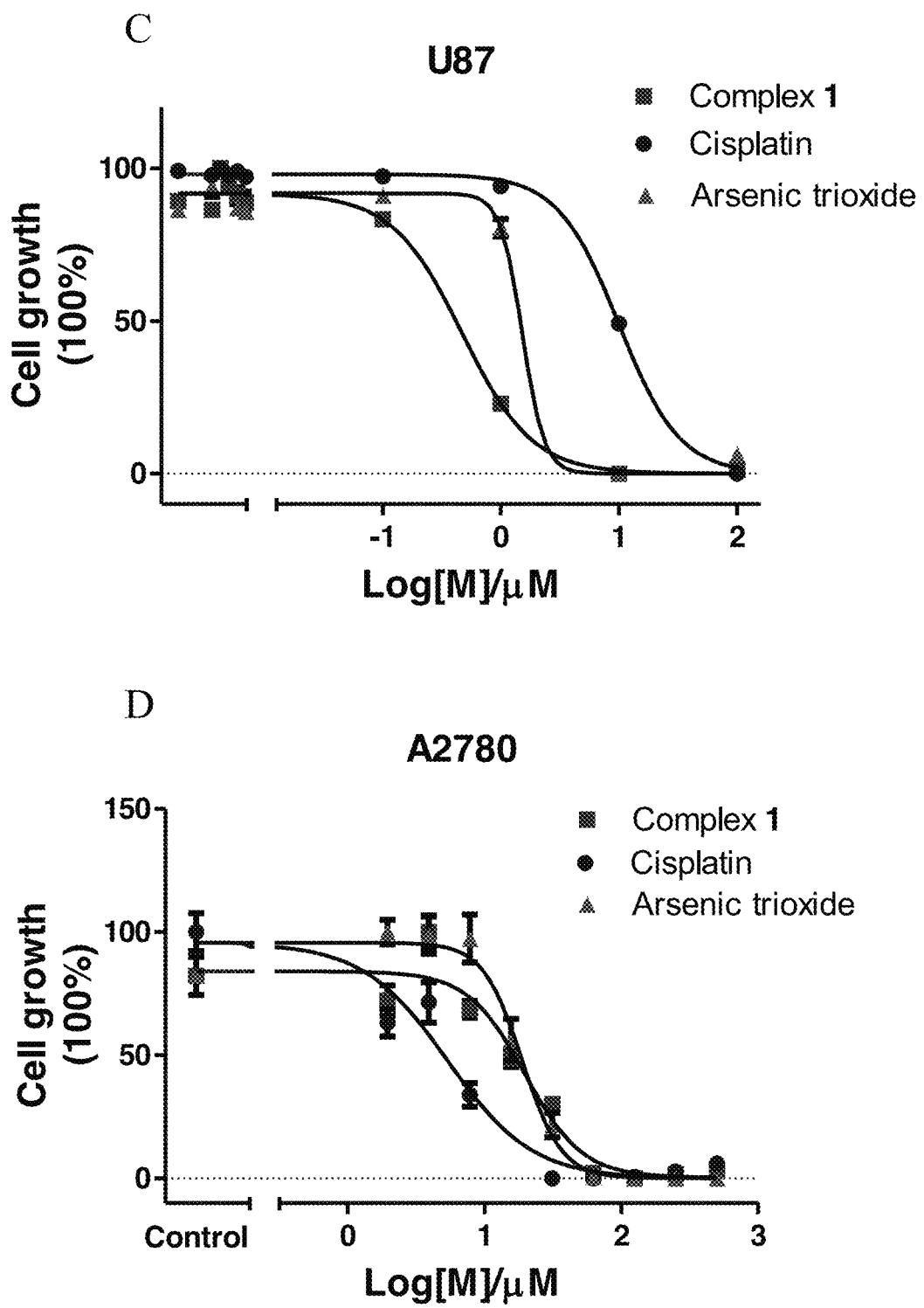
Figure 3:
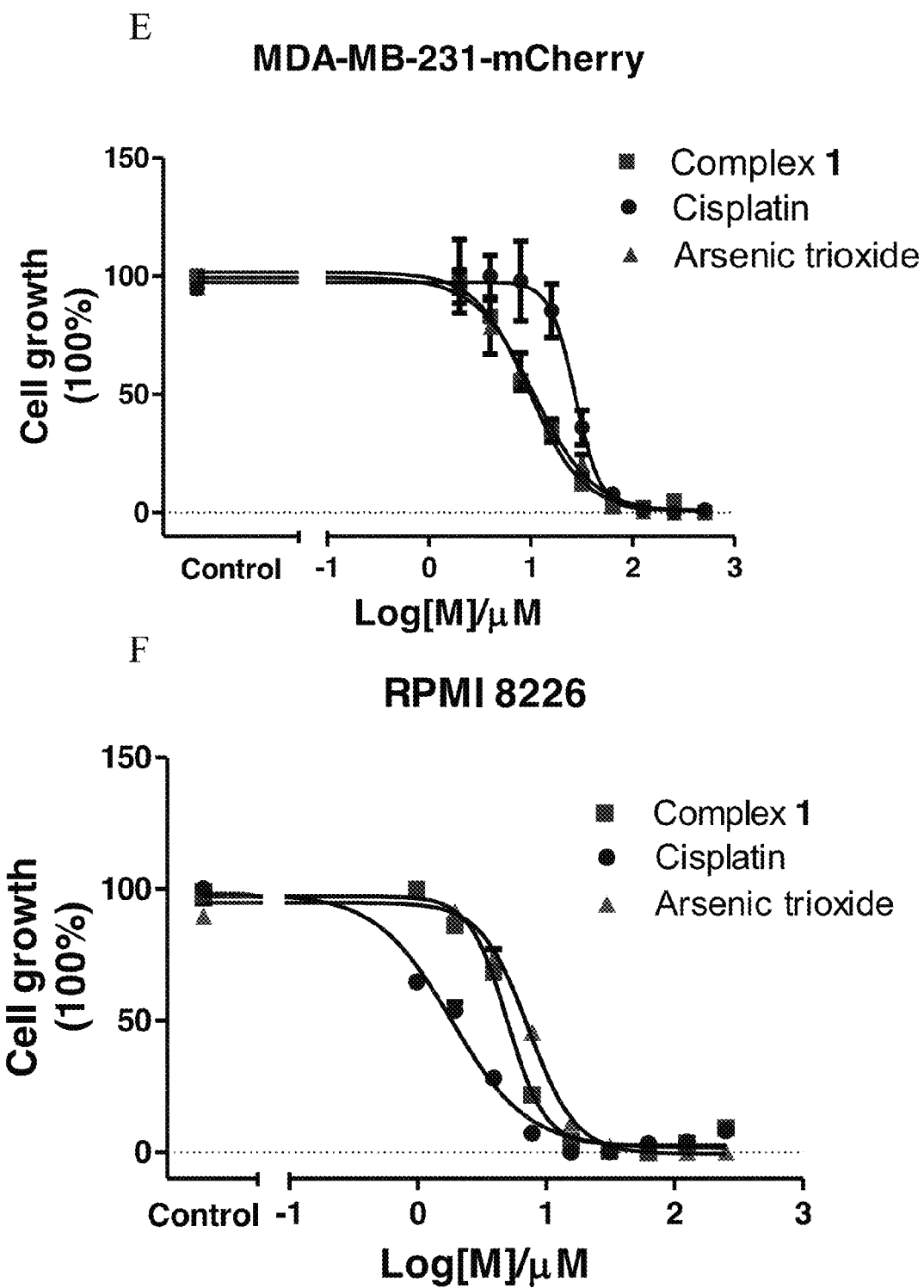

Compound (1) has showed better cytotoxic activity than either cisplatin or $As_2O_3$ in colon HCT-116 ($IC_{50}$=1.6±0.4 µM vs. 5.5±1.3 µM and 9.4±0.9 µM) and glioblastoma U-87 ($IC_{50}$=0.37±0.11 µM vs. 9.6±0.8 µM and 1.6±2.9 µM) cancer cell lines (FIG. 3 and Example 22, Table 8). Additionally, compound (1) showed twice the cytotoxicity of cisplatin against MDA-MB-231-mCherry cells ($IC_{50}$=9.5±0.1 µM and 22.3±2.8 µM), as well as improved cytotoxicity compared with $As_2O_3$ in RPMI 8226 multiple myeloma cells ($IC_{50}$=4.5±1.0 µM vs. 7.1±0.2 µM, Table 8).

Trans-platinum compounds in comparison with cis-compounds display different patterns of ligand substitution, which contributes to the potency of trans-platinum compounds in cisplatin-resistant cell lines. The distinct biological activity of compound (1) and related compounds in vitro may be the result of the strong trans effect of the $As(OH)_2$ moiety combined with the trans stereochemistry of the N-atoms at the platinum center.

The present disclosed contemplates conjugates of the disclosed compounds coupled to at least one ligand. Suitable ligands include an amino acid, a peptide, a protein, a glycan, a peptidoglycan, a polysaccharide, or an oligonucleotide. Such ligands form conjugates with the disclosed compounds by coordinating with M, where M is Pt, Pd or Ni. Coordination with M can occur via N-bonded, S-bonded, O-bonded or P-bonded coordinations. Alternatively, one of $R^1$-$R^9$ may be derivatized to enable covalent bond formation with the ligand. Two exemplary ligand conjugate methods are described in detail below, though one skilled in the art would recognize similar conjugate chemistry is known for coupling other ligands described herein.

Polypeptide Conjugates

The disclosure encompasses peptide conjugates with the disclosed compounds. For example, cysteine residues can be reacted, forming disulfide bonds that cross-link protein to one or more ligands of the disclosed compounds. If the protein does not contain cysteine residues, the protein may be modified with 2-iminothiolane (Traut's reagent) using the chemical scheme (7) shown below.

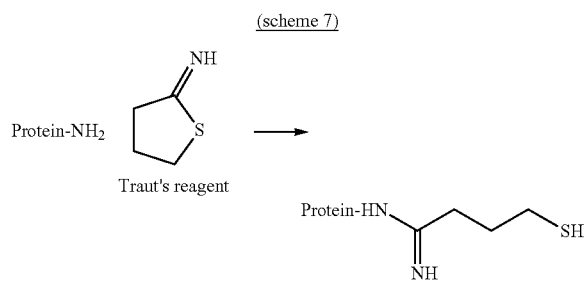

The latter embodiment provide a S-bonded ligand that can coordinate to M of the disclosed compounds, wherein M is Pt, Pd or Ni. Alternatively, the resultant ligand can be used to couple to other moieties of the disclosed compounds, such as suitably activated $R^1$-$R^9$ groups as such groups exist in the disclosed compounds. Such embodiments may be advantageous in particular contexts where preservation of the protein may serve an important secondary function, such as ligand-mediated targeting of the disclosed compounds to ligand-specific receptors located on surfaces of specific cell types such as cancer cells.

One versatile feature of many embodiments of compound-protein conjugates is that the native structure of the protein is not absolutely critical for compound-protein conjugate fabrication. As described previously, stable compound-protein conjugate formation depends only upon the presence of reactive sulfhydryl groups in the protein for the purposes of cross-linking to the disclosed compounds.

The compound conjugates can be derivatized to vary the in vivo pharmacokinetics and biodistribution of compound conjugates. Towards this goal, compound conjugates can include, but are not limited to, polyethylene glycol chains (PEG) (to extend the lifetime of the compound conjugates in the blood pool), membrane receptor ligands (e.g., folate, hemes, steroids, neurotransmitters, piperidine-based sigma receptor ligands), bioactive peptides, and even antibody chains. In these examples, the ligand of interest is covalently-attached to the disclosed conjugates through side chains of amino acid residues coordinated to M, wherein M is Pt, Pd or Ni, or to one of the $R^1$-$R^9$ moieties.

The availability of numerous functionalizable side groups in proteins makes it possible to fabricate protein-compound conjugates. Only three requirements for surface modification of side group functionality must be met. First, some of the side chains of the amino acids that form the protein must be accessible to solvent to undergo reaction with the modification chemistry. Side chains groups that are buried within the interior of the protein or that lie within the protein tertiary structure may not be solvent accessible to the modification chemistry. Second, and related to the first requirement, the target functionality of the side chain must not reside in an environment of secondary or tertiary structure that may sterically hinder the reaction with the modification chemistry. Third, and most importantly, the functionality of the side group must remain chemically reactive to permit conjugation with the disclosed compound(s).

If present, the free sulfhydryl group of an available cysteine may form mixed disulfide derivatives with other thiol-containing compounds, such as other disulfide compounds. Alternatively, cysteine sulfhydryl functionality may serve as a nucleophile to react with a halide-containing compound, such as an alkyl halide or a haloacetamide, or with a maleimide to form a thioether.

Although the chemical reactivity of alcohol hydroxyl groups of threonine, serine, and tyrosine is low in aqueous solution, these groups may be selectively modified, especially if they are reactive groups within enzyme active sites. Certain N-terminal seine or threonine groups that exist in a non-acylated form in proteins may be oxidized with periodate to yield aldehydes, which can be modified with a variety of amine or hydrazine derivatives. Still other alcohol hydroxyl groups can be selectively modified, like the tripeptide sequences of certain peptides wherein serine, threonine or tyrosine residues are separated from a histidine residue by a single amino acid (e.g., Ser-X-His, Thr-X-His and Tyr-X-His), by succinimidyl or sulfosuccinimidyl esters or by N-succinimidyl-3-(4-hydroxy-5-[$^{125}$I]iodophenyl) propionate (Bolton-Hunter reagent).

The alcohol functionality of tyrosine may be selectively modified in several ways. As an indirect method, these groups may be subjected to an initial nitration of the ortho position of its phenol using tetranitromethane, followed by reduction of the o-nitrotyrosine with sodium dithionite ($Na_2S_2O_4$) to form an o-aminotyrosine. The resultant aromatic amine of o-aminotyrosine can react with most amine-reactive reagents. In another approach, the phenol group in tyrosine residues may be converted to salicylaldehyde derivatives, followed by a reaction of the resultant salicylaldehydes with amine or hydrazine derivatives to yield the modified protein surfaces.

The carboxylic groups of aspartate or glutamate may be coupled to hydrazines or amines in aqueous solution using water-soluble carbodiimides such as 1-ethyl-3-(3-dimethylaminopropyl)-carbodiimide (EDAC). Including N-hydroxysuccinamide or N-hydroxysulfosuccinimide in the reaction mixture may improve the coupling efficiency of EDAC-mediated protein-carboxylic acid conjugations. To reduce intra- and inter-protein coupling to lysine residues, which is a common side reaction, carbodiimide-mediated coupling may be performed in a concentrated protein solution at a low pH, using a large excess of the nucleophile.

The amine groups of lysine, glutamine, and arginine may form amide linkages following coupling to reactive ester compounds. Alternatively, these amine groups may serve as general nucleophiles with compounds having appropriate leaving group reactive chemistry, such as alkyl halides or maleimides.

Photochemical reagents may represent an alternative strategy for modifying the surfaces of polypeptides for conjugation to the disclosed compound(s). Particularly useful for the present disclosure are multi-functional photoreagents having at least one photoreactive functionality and at least one non-photoreactive chemical functionality. Examples of groups with a photoreactive functionality include awl azides and benzophenone derivatives. Examples of groups with a non-photoreactive chemical functionality include sulthydryls, amines, alcohols, esters, carbonyls, carboxylates, and halides. The photoreagent may be coupled to a polypeptide using an irradiation source corresponding to the $\lambda_{max}$ of the photoreactive species. The photoreaction may proceed by a radical reaction, wherein the photoreactive species forms a covalent bond with any amino acid residue in the protein. The photoreactive species may form covalent bonds with tyrosine, phenylalanine, or tryptophan of the polypeptide, should the wavelength of excitation overlap the respective $\lambda_{max}$ of the photoreactive species and the $\lambda_{max}$ of any of these amino acid residues. Subsequent conjugation to the disclosed compound(s) may be effected using the secondary chemical functionality attached to the photoreagent.

Modification of disclosed compound(s) allows for prolonged circulation in the case of polyethylene glycol (PEG) attachment, and surface recognition in the case of folate and antibodies attachment. "Polyethylene glycol" includes polymers of ethylene glycol, and moieties and compounds containing —($CH_2CH_2O$)— units, preferably with a mass of at least 150 daltons, preferably at least 3,000 daltons.

Polyethylene glycol (PEG) may be covalently attached to amine or hydroxyl groups of $R^1$-$R^9$ of the disclosed compounds. The amino moiety of lysine and glutamine resides can be modified to introduce functionality such as the polyethylene glycol (PEG) group. Likewise, the hydroxyl moiety of serine, threonine, and tyrosine may be modified to introduce similar functionality as observed with the amino moiety. The introduction of the PEG group may be done via a coupling reaction with cyanuric chloride, which is reactive with both amino and hydroxyl moieties. The reaction scheme (8) with an amine moiety on the cross-linked polypeptide is shown below.

(scheme 8)

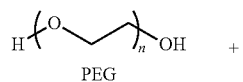

PEG

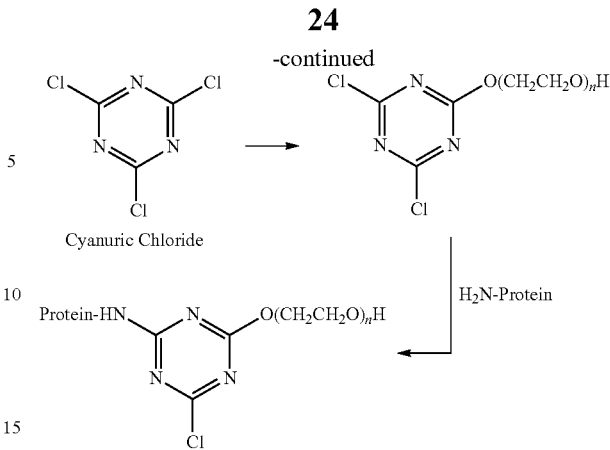

Surface modification using folate is an extension of the PEG surface modification method shown above. The folate in this instance may be activated using N-hydroxysuccinamide in a dicyclohexyl carbodiimide (DCC) coupling reaction. The activated folate then may be coupled to a PEG moiety containing an amino group functionality to form an amide bond between PEG and folate. This process is depicted below (scheme (9)). The resultant modified PEG can be attached to the surface of the disclosed compound(s) in the same manner as depicted above via a cyanuric chloride coupling reaction.

(scheme 9)

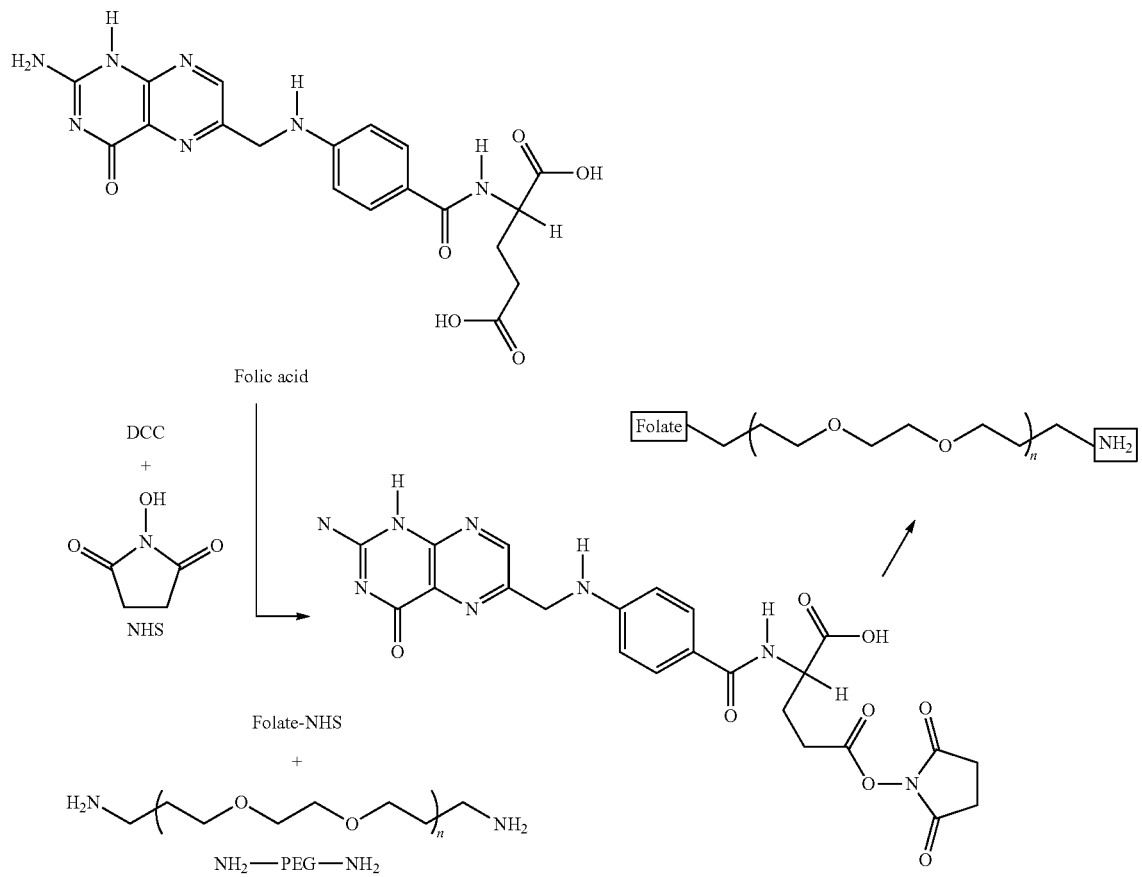

This example represents one embodiment whereby the disclosed compound(s) may be modified to contain any ligand using a combination of the preceding chemical reaction schemes. Thus, one may chemically attach PEG to the desired ligand using known coupling chemistry. The PEG-ligand derivative is then coupled to cyanuric chloride and the resultant cyanuric-PEG-ligand compound is reacted with available amines of the polypeptide to yield the desired surface modifications. Although the preceding reaction schemes may permit mono-substituted PEG derivatives to be attached at each site of modification in the polypeptide, the presence of three functionally reactive chlorines in cyanuric chloride may allow for more extensive coupling with the PEG derivative. The use of cyanuric chloride may be advantageous in those cases where each surface modification on polypeptide may bear a di-substituted PEG derivative. Optionally, one may use any bifunctional protein crosslinking reagent instead of cyanuric chloride and react the resultant PEG-ligand compound with any type of nucleophile present on the polypepide.

The conjugation of folate to the disclosed compounds allows targeting to folate-binding tumor cells. Ovarian, breast, and human nasopharyngeal tumors all possess a high concentration of folate receptors on their surface. Liposomes modified by folate-PEG conjugates target folate receptor bearing KB tumor cells and exhibit an inhibitory effect on their growth. Specifically, these types of agents are expected to target induced squamous cell carcinoma with the folate-modified compounds. Similarly, many oral and upper gastrointestinal tract tumors have a high affinity for various hemes (which greatly assists in the use of hematoporphyrins as photodynamic therapy agents). Polypeptides with surface hemes attached to the disclosed compound(s) may also be used to target induced squamous cell carcinoma.

The modification of the disclosed compounds with immunoglobulins allows targeting of T-cell receptors. This modification may be carried out using monoclonal antibodies that are specific for T-cell receptors. These monoclonal antibodies may be covalently coupled to the disclosed compounds via a dimethylaminopropyl-carbodiimide hydrochloride (EDC) coupling reaction according to scheme (10).

through reaction with EDC. The monomeric forms of the protein containing EDC-activated carboxylic ester on its surface may be purified and subsequently reacted with a suitably derivatized $R^1$-$R^9$ of the disclosed compounds. The lysine amino moiety of the polypeptide-compound conjugate surface forms a covalent isopeptide bond with a glutamate residue in target antibody protein. Optionally, the order of the reactions may be reversed wherein EDC is initially reacted with carboxylic acid moieties in amino acid residues of the cross-linked polypepide-compound conjugate, followed by secondary reaction with lysine moieties in amino acid residues of the antibody protein ligand to form the compound conjugated with an antibody. In this fashion, the coupling reaction may be used to covalently like the disclosed compounds to any protein that contains available carboxylic acid or amino moieties. Furthermore, carboxylate moieties on the protein my be used for surface modification by reaction with amines, or by esterification.

Oligonucleotide Conjugates

The disclosure encompasses oligonucleotide conjugates that include the disclosed compounds. For example, oligonucleotides can be prepared that contain phosphorothiolate groups at one or more internucleotidyl phosphate linkages. The sulfur moiety of the phosphorothiolate can form an S-bond with M of the disclosed compounds, wherein M is Pt, Pd or Ni. Alternatively, the sulfur moiety can be used to conjugate to one of suitably derivatized $R^1$-$R^9$ groups of the disclosed compounds. Furthermore, modifications can be introduced into the terminal positions of oligonucleotides during their synthesis, wherein the modifications include one or more of an amine or a sulfur. The resultant oligonucleotides so modified to contain an amine group can be used for form an N-bond with M of the disclosed compounds, wherein M is Pt, Pd or Ni. Alternatively, the amine moiety can be used to conjugate to one of suitably derivatized $R^1$-$R^9$ groups of the disclosed compounds. For those oligonucleotides that include terminal modifications that introduce a sulfur group, then conjugates containing the disclosed compounds coupled to the resulting oligonucleotides can be prepared as described supra, wherein the sulfur group can form an S-bond to M of the disclosed compounds, (scheme 10)

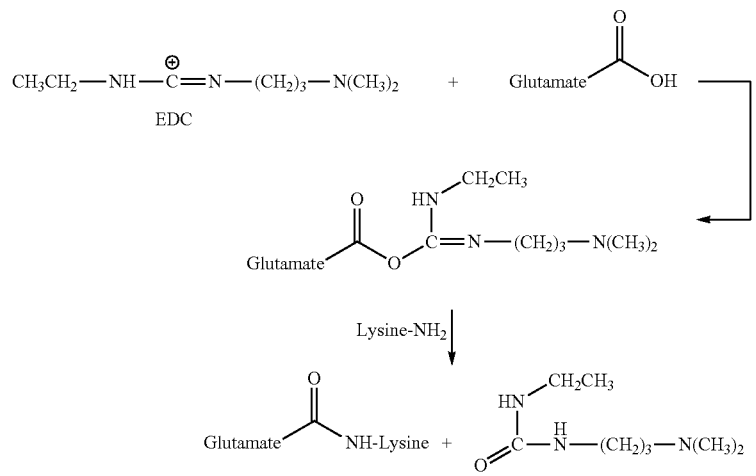

In this coupling reaction, the carboxylic acid moiety of a glutamate residue in the protein to be attached to one or more of the disclosed compound(s) may be activated wherein M is Pt, Pd or Ni, or wherein the sulfur group can be used to conjugate to one of suitably derivatized $R^1$-$R^9$ groups of the disclosed compounds.

Pharmaceutical Compositions

The present disclosure contemplates pharmaceutical compositions of preparations of the disclosed compound(s) for administration to mammals to treat cancer and related conditions. In a preferred embodiment, a composition for administration is a pharmaceutical composition, preferably in a single unit dosage form. Pharmaceutical compositions and single unit dosage forms can comprise a prophylacticly or therapeutically effective amount of one or more prophylactic or therapeutic agents, and a typically one or more pharmaceutically acceptable carriers or excipients or diluents.

The term "pharmaceutically acceptable" means approved by a regulatory agency of the Federal or a state government (for example, the U.S. Food and Drug Administration) or listed in the U.S. Pharmacopeia or other generally recognized pharmacopeia for use in animals, and more particularly in humans.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin. Pharmaceutical compositions can, but need not, comprise one or more active or inactive ingredients that are not necessarily considered pharmaceutically acceptable to current practitioners in the art.

A pharmaceutical composition can be administered by any mute according to the judgment of those of skill in the art, including but not limited to orally, intravenously, intragastrically, intraduodenally, intraperitoneally or intracerebroventricularly.

Typical pharmaceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

The disclosure further encompasses administration of pharmaceutical compositions and single unit dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a preparation of the described compounds having anti-cancer effect, together with a suitable amount of carrier so as to provide the form for proper administration to the patient.

The formulation should suit the mode of administration. In a preferred embodiment, the pharmaceutical compositions and single unit dosage forms are sterile and prepared in a form suitable for administration to a subject, preferably an animal subject, more preferably a mammalian subject, and most preferably a human subject. Besides humans, preferred animal subjects include horses, birds, cats, dogs, rats, hamsters, mice, guinea pigs, cows, and pigs.

A pharmaceutical composition of the invention is formulated to be compatible with its intended mute of administration. Examples of mutes of administration include, but are not limited to, parenteral, e.g., intravenous, intradermal, subcutaneous, intramuscular, subcutaneous, oral, buccal, sublingual, inhalation, intranasal, transdermal, topical, transmucosal, intra-tumoral, intra-synovial and rectal administration. In a specific embodiment, the composition is formulated in accordance with routine procedures as a pharmaceutical composition adapted for intravenous, subcutaneous, intramuscular, oral, intranasal or topical administration to human beings. In an embodiment, a pharmaceutical composition is formulated in accordance with routine procedures for oral administration to human beings. Typically, compositions for oral administration are solid dosage forms or solutions in sterile isotonic aqueous buffer.

Examples of dosage forms include, but are not limited to: tablets; caplets; capsules, such as soft elastic gelatin capsules or hard capsules; dropping pills; cachets; troches; lozenges; dispersions; suppositories; ointments; cataplasms (poultices); pastes; powders; dressings; creams; plasters; solutions; patches; aerosols (for example, nasal sprays or inhalers); gels; liquid dosage forms suitable for oral or mucosal administration to a patient, including suspensions (for example, aqueous or non-aqueous liquid suspensions, oil-in-water emulsions, or a water-in-oil liquid emulsions), solutions, and elixirs; liquid dosage forms suitable for parenteral or intravenous administration to a patient; and sterile solids (for example, crystalline or amorphous solids or granular forms) that can be reconstituted to provide liquid dosage forms suitable for parenteral or intravenous administration to a patient.

The composition, shape, and type of dosage forms of a preparation of the described compounds will typically vary depending on their use. For example, a dosage form used in the acute treatment of a cancer or related disorder may contain larger amounts of one or more of a preparation of the disclosed compounds than a dosage form used in the chronic treatment of the same disease. Also, the therapeutically effective dosage form may vary among different types of diseases or disorders. Similarly, a parenteral dosage form may contain smaller amounts of one or more of the active than an oral dosage form used to treat the same disease or disorder. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

Generally, the ingredients of compositions comprising a preparation of the disclosed compounds are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Pharmaceutical compositions used in the methods of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

In certain embodiments, the oral dosage forms are solid and prepared under anhydrous conditions with anhydrous ingredients, as described in detail in the sections above. However, the scope of the invention extends beyond anhydrous, solid oral dosage forms. As such, further forms are described herein.

Typical oral dosage forms are prepared by combining the active ingredient(s) (that is, a preparation of the he disclosed compound(s)) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

The amount of the composition in the methods of the invention which will be effective in the prevention, treatment, management, or amelioration of a cancer disorder or one or more symptoms thereof will vary with the nature and severity of the disease or condition, and the mute by which the active ingredient is administered. The frequency and dosage will also vary according to factors specific for each patient depending on the specific therapy (e.g., therapeutic or prophylactic agents) administered, the severity of the disorder, disease, or condition, the mute of administration, as well as age, body, weight, response, and the past medical history of the patient. Effective doses may be extrapolated from dose-response curves derived from in vitro or animal model test systems.

Typical dosage forms for administration in methods of the invention comprise a composition of the invention in an amount within the range of from about 0.001 mg to about 500 mg of the disclosed compounds per day, 0.10 mg to 300 mg of the disclosed compounds per day, or 1.0 mg to 200 mg of the disclosed compounds per day given as a single once-a-day dose or as divided doses throughout the day. Particular dosage forms of the invention have incremental variations from about 0.001, 0.01, 0.1, 0.2, 0.25, 0.3, 0.5, 0.75, 1.0, 2.0, 2.5, 3.0, 5.0, 7.5, 10.0, 15.0, 20.0, 25.0, 40.0, 50.0, 60.0, 75.0, 100, 125, 150, 175, 200, 250, 300, 400, and 500 mg of the disclosed compounds, as well as incremental dosage variations thereof.

Exemplary dosage forms of the invention having a liquid formulation include 1, 3, 5, 7.5, 10, 15, 20, 50, 75, and 100 ml of a liquid composition of the disclosed compounds having a concentration ranging from about 0.01 μg/ml to about 500 mg/ml. The preferred concentrations of such liquid compositions will depend upon the dissolution characteristics of the medium, which will determine the upper limit of pharmaceutically acceptable concentrations of the disclosed compounds in such compositions. Consequently, alternative, pharmaceutically acceptable, concentrations of the disclosed compounds in liquid compositions that are lower, as well as higher, than that stated herein are also contemplated by the present invention.

In the case of liquid dosage forms, suitable concentrations of the disclosed compounds are suspended or dissolved in pharmaceutically acceptable carrier media, such as water, saline, and the like. Furthermore, suitable concentrations of the disclosed compounds are suspended or dissolved under physiologically and physiochemically appropriate conditions.

As explained in the disclosure, certain of the disclosed compounds differ in their hydrophobicity, thereby rendering them insoluble, slightly soluble, moderately soluble, very soluble or highly soluble in a particular solvent system, such as aqueous solvents (for example, water or saline) or solvent systems (for example, water/DMSO or saline/DMSO). To the extent that solubility presents a barrier to providing adequate ADME properties for the delivery system or mute of administration for certain of the disclosed compounds, particle size reduction of the disclosed compounds to increase solvent-accessible surface area and solvation potential can improve solubility of the disclosed compounds having hydrophobic properties. Methods, techniques and instrumentation are known in the art for achieving particle size reduction (for example, micronization) can be useful for achieving particle size reduction for the disclosed compounds.

Exemplary doses of a composition of the disclosed compounds include microgram or milligram amounts of the disclosed compound(s) per kilogram of subject or sample weight. For a composition used in the invention, the dosage administered to a patient can be administered from about 0.001 mg/kg to about 10 mg/kg. In certain embodiments, the dosage can be from about 0.02 mg/kg to about 4.0 mg/kg of the patient's body weight, based on weight and purity of a preparation the disclosed compound(s) in the composition.

The composition can be administered as a single once-a-day dose or as divided doses throughout a day. In some embodiments, the daily dose is administered twice daily in equally divided doses. In other embodiments, the daily dose is administered three times per day. In particular embodiments, the daily dose is administered three times per day in equally divided doses. In particular embodiments, the daily dose is administered four times per day in equally divided doses. The actual dosage can be determined by a practitioner of skill in the art according to, for example, the subjects age, body weight, body mass index, or other factors. In certain embodiments, administration of a composition in the invention may be repeated daily. In certain embodiments and the administrations may be separated by at least 1 day, 2 days or 3 days.

An effective amount of a composition described herein will provide therapeutic benefit without causing substantial toxicity. Toxicity of a composition can be determined by standard pharmaceutical procedures in cell cultures or experimental animals, for example, by determining the $LD_{50}$ (that is, the dose lethal to 50% of the population) or the $LD_{100}$ (that is, the dose lethal to 100% of the population).

The therapeutic index is the dose ratio between therapeutic effect and toxicity effect. Compounds which exhibit high therapeutic indices are preferred. The data obtained from these cell culture assays and animal studies can be used in formulating a dosage range that is not toxic for use in humans. The dosage of the compounds described herein lies preferably within a range of circulating concentrations that include the effective dose with little or no toxicity. The dosage may vary within this range depending upon the dosage form employed and the route of administration utilized. The exact formulation, mute of administration and dosage can be chosen by the individual physician in view of the patient's condition and the indication to be treated. (See, e.g., Fingl et al., 1996, In: The Pharmacological Basis of Therapeutics, $9^{th}$ ed., Chapter 2, p. 29, Elliot M. Ross).

The descriptions of exemplary doses are merely alternative descriptions that may be used optionally at the discretion of the physician and are not intended to conflict or supersede other descriptions of doses disclosed herein. The pharmacological action of preparations of the disclosed compounds is demonstrated by the disclosed biological examples.

EXAMPLES

Example 1

General Methods

Cisplatin, $K_2[PtCl_4]$, DMSO, methanol, acetonitrile, propionitrile and $As_2O_3$ were purchased from Sigma-Aldrich and used without further purification. Media for the cell cultures and all other cell supplements were purchased from Invitrogen. The following spectrometers were used: NMR: Bruker Avance-III 600 and 500 MHz; chemical shifts ($^1H$, $^{13}C$) were referenced to tetramethylsilane at 0.000 ppm $^1H$ and $^{13}C$ if it was present, and to residual solvent signal for samples in which TMS was absent (for [$D_6$]DMSO, $\delta_H$=2.50 ppm and $\delta_C$=39.5 ppm). The $^{195}Pt$ (129 MHz) and $^{15}N$ (61 MHz) NMR spectra were acquired on a 600 MHz Bruker Avance III spectrometer equipped with BBO (broadband observe) probe. $^{195}Pt$ NMR chemical shifts were referenced indirectly to TMS in $^1H$ NMR spectrum such that N $^{195}PtCl_6$ in $D_2O$ would resonate at 0.0 ppm. $^{15}N$ NMR chemical shifts, both those observed directly in $^{15}N$-detect 1D experiments and 2D $^1H$-$^{15}N$ HSQC experiments, were referenced indirectly to TMS in the $^1H$ spectra, such that $^{15}NH_4Cl$ would resonate at 0.0 ppm. The $^{195}Pt$ NMR spectra were acquired with the simple zg pulse sequence, using an acquisition time of 0.020 sec, and a relaxation delay of 0.1 sec. Spectra acquired for the variable temperature (VT) experiments involved setting the temperature to a particular value (in 5-degree increments), waiting 15 minutes for equilibration, calibrating the temperature using a neat ethylene glycol temperature calibration standard, inserting the sample of interest, equilibrating it for five minutes, then acquiring a 24-scan $^1H$ spectrum employing a 90° pulse and a 30-second D1 delay for relaxation, ensuring accurate peak integration. Data were acquired using Topspin 2.1.4. UV/Vis electron absorbance measurements were performed on a Perkin Elmer Lambda 650 spectrophotometer. IR: Bruker Tensor 37 FT-IR. Elemental analysis was performed at Prevalere, Life Sciences, LLC, Whitesboro, N.Y.

Example 2

Synthesis of compound (1) (arsenoplatin, [Pt(μ-NHC($CH_3$)O)$_2$ClAs(OH)$_2$])

Cisplatin (300 mg, 1.00 mmol) or $K_2[PtCl_4]$ (415 mg, 1.00 mmol) was added to 125 $cm^3$ of 9:1 $CH_3CN/H_2O$ (v/v).

The mixture was stirred at 90° C. Once the platinum compound was dissolved, 396 mg $As_2O_3$ (2.00 mmol) was added to the solution, and the reaction mixture was stirred at 90° C. for 72 hours. The resulting mixture was filtered, and the filtrate was left at room temperature in a glass beaker for approximately 4 weeks until crystals formed. Crystals suitable for a single crystal X-ray analysis were retrieved from solution. The solution was filtered, washed with $CH_3CN:H_2O$ (9:1 mixture), and the obtained crystals were dried in a dessicator. Yield 350 mg product (75%; 23% when cisplatin is used). Complex is soluble in DMSO, methanol, ethanol, and partially in water. Elemental analysis (% calcd., found for $C_7H_{18.5}AsClN_{3.5}O_6Pt$): C, (15.20, 15.24); H, (3.37, 3.36); N, (8.86, 8.69). NMR: $^1H$ NMR (600 MHz, $[D_6]DMSO$, 25° C.) δ: 8.91 (s, 2H—OH), 8.15 (s, 2H—NH), 2.13 (s, 6H—$CH_3$). $^{13}C$ NMR (150 MHz, $[D_6]$DMSO, 25° C.): δ 172.1 (C-1, C-3), 171.4 (C-5, C-7), 22.5 (C-6, C-8), 16.6 (C-2, C-4). $^{15}N$ NMR (60 MHz, from the $^1H$-$^{15}N$ HSQC, $[D_6]$DMSO, referenced to $^{15}NH_4Cl$, 25° C.): 8106.4 (N-1, N-2), $^{195}Pt$ NMR (129 MHz, $[D_6]$DMSO, 25° C.), δ: −3589 (s, 1Pt) ppm. UV/Vis ((methanol-water=1:1): $λ_1$=283 nm (ϵ=4062 $dm^3$ $mol^{-1}$ $cm^{-1}$), $λ_2$=247 nm (ϵ=3621 $dm^3$ $mol^{-1}$ $cm^{-1}$), sh. 260 nm.

Example 3

Synthesis of compound (2) ($[Pt(μ-NHC(CH_3CH_2)O)_2ClAs(OH)_2]$)

$K_2[PtCl_4]$ (415 mg, 1.00 mmol) was added to 50 $cm^3$ of 9:1 $H_2O$/propionitrile (v/v). The mixture was stirred at mom temperature. Once the platinum compound was dissolved, 396 mg $As_2O_3$ (2.00 mmol) of the reaction mixture was stirred at room temperature for 96 hours.

LC/ESI-MS data were recorded every 24 hours. The color gradually turned yellow and ultimately colorless over the 4 day period. The resulting mixture was filtered and left to sit (pH roughly 2) at 25° C., and, within a week, crystals suitable for single crystal X-ray analysis appeared. The solution was filtered again, washed with $H_2O$, dried, and weighed (212 mg, 44%). Compound (2) is soluble in methanol, DMSO, and partially soluble in $H_2O$.

Elemental analysis (% calcd., found for $C_6H_{14}AsClN_2O_4Pt$): C, (14.90, 14.80); H, (2.92, 2.60); N, (5.79, 5.82). NMR: $^1H$ NMR (500 MHz, $[D_6]$DMSO): δ 8.91 (s, 2H—OH), 8.04 (s, 2H—NH), 2.47 (q, J=7.6 Hz, 4H—$CH_2$,), 1.04 (t, J=7.6 Hz, 6H—$CH_3$). $^{13}C$ NMR (125 MHz, $[D_6]$DMSO): δ 175.0, 24.1, 11.3 ppm. UV/Vis ((methanol-water=1:1 v/v): $∥_1$=285 nm, $λ_2$=245 nm.

Example 4

Synthesis of compound (5) ($[Pt(μ-NHC(CH_3)O)_2(SCN)As(OH)_2]$)

Compound (1) obtained in Example 2 (100 mg, 0.18 mmol) was dissolved in 4 $cm^3$ of methanol and added to an equal-molar solution of KSCN (17.6 mg, 0.180 mmol) in 4 $cm^3$ of water. The reaction mixture was allowed to stir at 50° C. for 5 hours. The mixture was filtered and the solution was left standing at mom temperature until crystals appeared. The obtained crystals were removed by filtration. Yield: 60.00 mg (52%). Elemental analysis (% calcd., found for $PtC_5H_{10}N_3O_4SAs$): C, (12.56, 12.37); H, (2.11, 1.97); N, (8.78, 8.56). NMR data: $^1H$ NMR (600 MHz, $[D_6]$DMSO): δ 2.21 (s, 6H, $CH_3$), 7.70 (s, 2H, NH), 9.20 (s, 2H, OH). $^{13}C$ NMR (150 MHz, $[D_6]$DMSO) 817.5 ($CH_3$), 117.7 (SCN), 172.6 (CO); $^{195}Pt$ NMR (129 MHz, $[D_6]$DMSO) δ −3861 ppm (s, 1Pt); UV/Vis (methanol-water=1:1): $∥_1$=285 nm (E=4217 $dm^3$ $mol^{-1}$ $cm^{-1}$); $λ_2$=225 nm (E=15919 $dm^3$ $mol^{-1}$ $cm^{-1}$), shoulder at 265 nm. Solubility: DMSO and methanol.

Example 5

Synthesis of compound (6) ($[Pt(μ-NHC(CH_3)O)_2(NCS)As(OH)_2]$)

Compound (5) obtained in Example 4 was dissolved in DMSO solution at room temperature. Isomerization of Compound (5) occurred. NMR data: $^1H$ NMR (600 MHz, $[D_6]$DMSO): δ 2.17 (s, 6H, $CH_3$), 8.57 (s, 2H, NH), 9.11 (s, 2H, OH). $^{13}C$ NMR (150 MHz, $[D_6]$DMSO) 816.4 ($CH_3$), 134.4 (NCS), 172.7 (CO). $^{195}Pt$ NMR (129 MHz, $[D_6]$DMSO) δ −3724 ppm (s, 1Pt). $^{15}N$ NMR (60 MHz, from the $^1H$-$^{15}N$ 2D HSQC and $^{15}N$-detect 1D of the sample isotopically labeled with $S^{13}C^{15}N$, $[D_6]$DMSO): δ 105.8 (N-1, N-2), 91.5 ppm (SCN).

Example 6

Synthesis of compound (7) ($[Pt(μ-NHC(CH_3CH_2)O)_2(SCN)As(OH)_2]$)

Compound (2) obtained in Example 3 (96.72 mg, 0.2 mmol) was dissolved in 4 $cm^3$ of methanol and added to an equal-molar solution of KSCN (19.44 mg, 0.2 mmol) in 4 $cm^3$ of water. The reaction mixture was allowed to stir at 50° C. for 5 hours. The mixture was filtered and the solution was left standing at mom temperature until crystals appeared. The obtained crystals were removed by filtration. Yield: 37 mg (37%).

Example 7

Synthesis of compound (8) ($[Pt(μ-NHC(CH_3CH_2)O)_2(NCS)As(OH)_2]$)

Compound (7) obtained in Example 6 was dissolved in DMSO solution at room temperature. Isomerization of compound (7) occurred and both Compounds (7) and (8) are present in the solution.

Example 8

Synthesis of compound (9) ($[Pt(μ-NHC(CH_3)O)_2(Py)As(OH)_2]$)

Compound (1) obtained in Example 2 (100 mg, 0.18 mmol) was dissolved in 4 $cm^3$ of methanol and water mixture, and 14.6 μL of pyridine and 22.1 mg of $NaClO_4$ were added. The reaction mixture was allowed to stir at room temperature over night. HRMS spectrum indicated presence of $M^+$ ion at 498 m/z.

Example 9

Synthesis of compound (10) ($[Pt(μ-NHC(CH_3)O)_2ClAs(OH)(OCH_3)]$)

Compound (1) obtained in Example 2 (100 mg, 0.18 mmol) was dissolved in 4 $cm^3$ of anhydrous methanol. HRMS spectrum indicates molecular ion at m/z 470 in the negative mode consistent with the structure of compound (10) was obtained.

Example 10

Synthesis of compound (3) ([Pt(μ-NHC(CH$_3$)O)$_2$IAs(OH)$_2$])

K$_2$[PtI$_4$] (780 mg, 1.00 mmol) will be dissolved in 125 cm$^3$ of 9:1 CH$_3$CN/H$_2$O (v/v). The mixture will be stirred at 90° C. Once the platinum complex is dissolved, 386 mg As$_2$O$_3$ (2.00 mmol) will be added to the solution, and the reaction mixture will be stirred at 90° C. for 72 hours.

Example 11

Synthesis of compound (4) ([Pt(μ-NHC(CH$_3$CH$_2$)O)$_2$IAs(OH)$_2$])

K$_2$[PtI$_4$] (780 mg, 1.00 mmol) will be dissolved in 125 cm$^3$ of 1:9 CH$_3$CH$_2$CN/H$_2$O (v/v). Once the platinum complex is dissolved, 396 mg As$_2$O$_3$ (2.00 mmol) will be added to the solution, and the reaction mixture will be stirred at room temperature for four days.

Example 12

Synthesis of compound (11) ([Pd(μ-NHC(CH$_3$)O)$_2$ClAs(OH)$_2$])

K$_2$[PdCl$_4$] (326 mg, 1.00 mmol) will be dissolved in 125 cm$^3$ of 9:1 CH$_3$CN/H$_2$O (v/v). The mixture will be stirred at 90° C. Once the palladium complex is dissolved, 396 mg As$_2$O$_3$ (2.00 mmol) will be added to the solution, and the reaction mixture will be stirred at 90° C. for 72 hours.

Example 13

Synthesis of compound (12) ([Pd(μ-NHC(CH$_3$CH$_2$)O)$_2$ClAs(OH)$_2$])

K$_2$[PdCl$_4$] (326 mg, 1.00 mmol) will be dissolved in 125 cm$^3$ of 1:9 CH$_3$CH$_2$CN/H$_2$O (v/v). Once the palladium complex is dissolved, 396 mg As$_2$O$_3$ (2.00 mmol) will be added to the solution, and the reaction mixture will be stirred at mom temperature for four days.

Example 14

Synthesis of compound (13) ([Ni(μ-NHC(CH$_3$)O)$_2$ClAs(OH)$_2$])

K$_2$[NiCl$_4$] (288 mg, 1.00 mmol) will be dissolved in 125 cm$^3$ of 9:1 CH$_3$CN/H$_2$O (v/v). The mixture will be stirred at 90° C. Once the nickel complex is dissolved, 396 mg As$_2$O$_3$ (2.00 mmol) will be added to the solution, and the reaction mixture will be stirred at 90° C. for 72 hours.

Example 15

Synthesis of compound (14) ([Ni(μ-NHC(CH$_3$CH$_2$)O)$_2$ClAs(OH)$_2$])

K$_2$[NiCl$_4$] (288 mg, 1.00 mmol) will be dissolved in 125 cm$^3$ of 1:9 CH$_3$CH$_2$CN/H$_2$O (v/v). The mixture will be stirred at 90° C. Once the nickel complex is dissolved, 396 mg As$_2$O$_3$ (2.00 mmol) will be added to the solution, and the reaction mixture will be stirred at room temperature for four days.

Example 16

Synthesis of compound (15) ([Pt(μ-NHC(CH$_3$)O)$_2$ClSb(OH)$_2$])

K$_2$[PtCl$_4$] (415 mg, 1.00 mmol) will be dissolved in 125 cm$^3$ of 9:1 CH$_3$CN/H$_2$O (v/v). The mixture will be stirred at 90° C. Once the platinum complex is dissolved, 583 mg Sb$_2$O$_3$ (2.00 mmol) will be added to the solution, and the reaction mixture will be stirred at 90° C. for 72 hours.

Example 17

Synthesis of compound (16) ([Pd(μ-NHC(CH$_3$)O)$_2$ClSb(OH)$_2$])

K$_2$[PdCl$_4$] (326 mg, 1.00 mmol) will be dissolved in 125 cm$^3$ of 9:1 CH$_3$CN/H$_2$O (v/v). The mixture will be stirred at 90° C. Once the palladium complex is dissolved, 583 mg Sb$_2$O$_3$ (2.00 mmol) will be added to the solution, and the reaction mixture will be stirred at 90° C. for 72 hours.

Example 18

Synthesis of compound (17) ([Ni(μ-NHC(CH$_3$)O)$_2$ClSb(OH)$_2$])

K$_2$[NiCl$_4$] (288 mg, 1.00 mmol) will be dissolved in 125 cm$^3$ of 9:1 CH$_3$CN/H$_2$O (v/v). The mixture will be stirred at 90° C. Once the nickel complex is dissolved, 583 mg Sb$_2$O$_3$ (2.00 mmol) will be added to the solution, and the reaction mixture will be stirred at 90° C. for 72 hours.

Example 19

Synthesis of compound (18) ([Pt(u-NHC(CH$_3$)O)$_2$(Py)Sb(OH)$_2$])

Compound (15) obtained in Example 16 (502 mg, 1 mmol) will be dissolved in 4 cm$^3$ of methanol and water mixture, and 14.6 μL of pyridine and 22.1 mg of NaClO$_4$ will be added. The reaction mixture will be allowed to stir at mom temperature over night.

Example 20

Synthesis of compound (19) ([Pt(u-NHC(CH$_3$)O)$_2$(Thiophenol)Sb(OH)$_2$])

Compound (15) obtained in Example 16 (502 mg, 1 mmol) will be dissolved in 4 cm$^3$ of methanol and 102 μL of thiophenol (1 mmol) will be added. The reaction mixture will be allowed to stir at room temperature over night.

Example 21

Crystallographic Structure Determination and Refinement Details

Colorless crystals of compounds (1), (2) and (5) were mounted using oil (Infineum V8512) on a glass fiber. All measurements were made on a Broker APEX-II CCD area detector with graphite monochromated MoK\α radiation. The data were collected at a temperature of 100(2) K (1a, 2, and 3) and 111(2) K (1b), and integrated and corrected for decay and Lp effects using Broker APEX II software. Final unit cell parameters were obtained through a refinement of all observed reflections during data integration. A face-indexed absorption correction was performed via)(PREP. The structures were solved and refined using the SHELXTL suite of software. In the structure of compound (1) (crystal form 1a) the non-hydrogen atoms were refined anisotropically. There is an acetamide and water disordered over the inversion center. The hydrogen atoms on the water were not found in the difference map. The C8 atom (in 1a) and Ni (in 3) were restrained with Uij components approximate to isotropic behavior. Hydrogen atoms were included in idealized positions, but not refined. In the structure of 1b hydrogen atoms on the oxygen and nitrogen atoms were refined isotropically. Neutral atom scattering factors, the values for Df' and Df", and the values for the mass attenuation coefficients were taken from the usual tabulation. Anomalous dispersion effects were included in F$_{calc}$. Explanations for B alerts generated from CheckCif are discussed in the refine special details of the corresponding cif files.

Compound (1) can crystallize in two different crystal systems, triclinic with space group P-1 (1a) and monoclinic with space group P2(1)/n (1b).

Crystal data for 1a. $C_7H_{18.50}AsClN_{3.50}O_6Pt$, Mr=553.21, Mo—Kα radiation, wavelength 0.71073, T 100(2) K, colorless plate, 0.54×0.28×0.09 mm, triclinic, space group P-1, a=7.0806(2) Å, b=9.3782(2) Å, c=11.7356(2) Å, α=91.1400 (10)°, β=90.8840(10)°, γ=107.3030(10)°, V=743.68(3) Å$^3$, Z=2, $d_{calcd}$=2.470 gcm$^{-3}$, μ=11.847 mm$^{-1}$, F(000)=522, 21,678 reflections, 4,341 unique, $R_{int}$=0.0547, $R_1$=0.0215 [I>2σ(I)], wR$_2$=0.0591 (all data), GOF 1.037. Representative crystallographic data for 1a is presented in Tables 1 and 2.

TABLE 1

Selected bonds (Å) and angles (deg.) for 1a.

| | |
|---|---|
| Pt1 N1 2.000(3) | N2 Pt1 Cl1 92.36(11) |
| Pt1 N2 2.004(3) | As1 Pt1 Cl1 176.86(2) |
| Pt1 As1 2.2732(3) | O4 As1 O3 107.32(17) |
| Pt1 Cl1 2.3272(8) | O4 As1 O2 91.4(2) |
| As1 O4 1.721(3) | O3 As1 O2 87.09(13) |
| As1 O3 1.722(3) | O4 As1 O1 84.77(14) |
| As1 O2 1.968(3) | O3 As1 O1 91.14(11) |
| As1 O1 2.019(2) | O2 As1 O1 175.07(14) |
| O1 C1 1.302(4) | O4 As1 Pt1 128.95(12) |
| O2 C3 1.297(6) | O3 As1 Pt1 123.69(12) |
| N1 C1 1.302(4) | O2 As1 Pt1 92.69(12) |
| N2 C3 1.289(6) | O1 As1 Pt1 92.11(7) |
| N2 Pt1 As1 86.78(11) | C1 N1 Pt1 121.5(2) |
| N1 Pt1 Cl1 93.11(9) | N1 Pt1 As1 87.79(8) |

TABLE 2

Hydrogen bonds for 1a [Å and deg].

| D—H···A | [ARU] | d(D—H) | d(H···A) | d(D···A) | <DHA |
|---|---|---|---|---|---|
| N(1)—H(1)...O(5) | [2665.03] | 0.93(6) | 2.16(6) | 3.061(4) | 162(5) |
| N(2)—H(2)...O(7) | [1455.01] | 0.93(6) | 2.01(6) | 2.914(5) | 166(5) |
| N(2)—H(2)...O(6) | [2666.01] | 0.93(6) | 2.46(6) | 3.252(5) | 144(5) |
| O(3)—H3...O(5) | [1665.03] | 0.84 | 1.76 | 2.561(3) | 158 |
| N(3)—H(3A)...Cl(1) | [2665.02] | 0.87(4) | 2.53(4) | 3.390(3) | 168(4) |
| N(3)—H(3B)...O(1) | [2675.02] | 0.84(5) | 2.26(6) | 3.049(5) | 157(5) |
| O(4)—H(4)...O(6) | [1565.01] | 0.84 | 1.90 | 2.736(5) | 179 |
| O(4)—H(4)...O(7) | [2776.01] | 0.84 | 2.15 | 2.751(6) | 128 |
| N(4)—H(4D)...Cl(1) | [2666.02] | 0.88 | 2.72 | 3.368(6) | 131 |
| N(4)—H(4E)...O(3) | [2776.02] | 0.88 | 2.04 | 2.839(6) | 151 |
| C(4)—H(4B)...O(7) | [1455.01] | 0.98 | 2.38 | 3.242(8) | 146 |
| C(8)—H(8A)...O(2) | [2776.02] | 0.98 | 2.39 | 3.091(10) | 128 |

Translation of ARU-code to Equivalent Position Code: [1455.] = −1 + x, y, z; [2666.] = 1 − x, 1 − y, 1 − z; [2776.] = 2 − x, 2 − y, 1 − z; [2665.] = 1 − x, 1 − y, −z; [1665.] = 1 + x, 1 + y, z; [1565.] = x, 1 + y, z; [2675.] = 1 − x, 2 − y, −z.

Crystal data for 1b. $C_8H_{20}AsClN_4O_6Pt$, Mr=573.74, Mo—Kα radiation, wavelength 0.71073, T 111(2) K, colorless block, 0.41×0.14×0.10 mm, monoclinic, space group P2(1)/n, a=14.2328(2) Å, b=7.62430 (10) Å, c=16.6254(2) Å, β=111.1120(10)°, V=1683.01(4) Å$^3$, Z=4, $d_{calcd}$=2.264 gcm$^{-3}$, μ=10.475 mm$^{-1}$, F(000)=1088, 35,220 reflections, 4,900 unique, $R_{int}$=0.0280, $R_1$=0.0173 [I>8σ(I)], wR$_2$=0.0417 (all data), GOF 1.144. Representative crystallographic data for 1b is presented in Tables 3 and 4.

TABLE 3

Selected bonds (Å) and angles (deg.) for 1b.

| | |
|---|---|
| Pt1 N1 1.999(2) | N2 Pt1 As1 87.76(6) |
| Pt1 N2 2.004(2) | N1 Pt1 Cl1 91.90(6) |
| Pt1 As1 2.2729(2) | N2 Pt1 Cl1 92.82(6) |
| Pt1 Cl1 2.3328(6) | As1 Pt1 Cl1 179.275(18) |
| As1 O3 1.7182(19) | O3 As1 O4 105.94(10) |
| As1 O4 1.7201(19) | O3 As1 O2 91.03(8) |
| As1 O2 2.0124(17) | O4 As1 O2 87.16(8) |
| As1 O1 2.0150(17) | O3 As1 O1 84.98(9) |
| O1 C1 1.298(3) | O4 As1 O1 91.51(8) |
| O2 C3 1.310(3) | O2 As1 O1 175.29(7) |
| N1 C1 1.299(3) | O3 As1 Pt1 129.37(8) |
| N2 C3 1.301(3) | O4 As1 Pt1 124.68(7) |
| N1 Pt1 N2 175.08(8) | O2 As1 Pt1 92.30(5) |
| N1 Pt1 As1 87.53(6) | O1 As1 Pt1 92.18(5) |
| | C1 N1 Pt1 121.63(17) |

TABLE 4

Hydrogen bonds for 1b [Å and deg.].

| D—H···A | [ARU] | d(D—H) | d(H···A) | d(D···A) | <DHA |
|---|---|---|---|---|---|
| N(1)—H(1)...O(6) | [4454.03] | 0.89(3) | 2.06(3) | 2.922(3) | 163(4) |
| N(3)—H(3)NA...Cl(1) | [4455.01] | 0.88(4) | 2.45(4) | 3.282(3) | 160(3) |
| N(2)—H(2)...O(5) | [4554.02] | 0.83(4) | 2.16(4) | 2.976(3) | 170(3) |
| N(3)—H(3)NB...O(2) | [1556.1] | 0.87(5) | 2.24(5) | 3.056(3) | 156(4) |
| O(3)—H(3)...O(5) | [2545.02] | 0.62(4) | 1.98(5) | 2.602(3) | 175(6) |
| N4—H(4)NA...Cl(1) | [4555.01] | 0.74(3) | 2.59(3) | 3.316(3) | 172(3) |
| O(4)—H(4)...O(6) | [3666.03] | 0.91(5) | 1.74(5) | 2.639(3) | 167(4) |
| N(4)—H(4)NB...O(1) | [1656.01] | 0.88(4) | 2.29(4) | 3.087(3) | 150(3) |

TABLE 4-continued

Hydrogen bonds for 1b [Å and deg.].

| D—H···A | [ARU] | d(D—H) | d(H···A) | d(D···A) | <DHA |
|---|---|---|---|---|---|
| C(10)—H(10)A...Cl(1) | [2656.01] | 0.98 | 2.82 | 3.630(3) | 141 |
| C(10)—H(10)...O(3) | [3656.01] | 0.98 | 2.53 | 3.367(4) | 143 |

Translation of ARU-code to Equivalent Position Code: [4554.] = 1/2 + x, 1/2 − y, −1/2 + z; [4454.] = −1/2 + x, 1/2 − y, −1/2 + z; [3666.] = 1 − x, 1 − y, 1 − z; [2545.] = 1/2 − x, −1/2 + y, 1/2 − z; [4455.] = −1/2 + x, 1/2 − y, 1/2 + z; [1556.] = x, y, 1 + z; [3656.] = 1 − x, −y, 1 − z; [4555.] = 1/2 + x, 1/2 − y, 1/2 + z; [1656.] = 1 + x, y, 1 + z; [2656.] = 3/2 − x, 1/2 + y, 3/2 − z.

Crystal data for compound (2). $C_6H_{14}AsClN_2O_4Pt$, Mr=483.65, Mo—Kα radiation, wavelength 0.71073, T 100(2) K colorless plate, 0.326×0.271×0.02 mm, orthorhombic, space group Pbca, a=14.1727(5) Å, b=9.6476 (3) Å, c=17.2048 (6) Å, V=2352.46 (14) Å$^3$, Z=8, $d_{calcd}$=2.731 gcm$^{-3}$, μ=14.944 mm$^{-1}$, F(000)=1792, 43,536 reflections, 3424 unique, $R_{int}$=0.0692, $R_1$=0.0243 [I>2σ(I)], $wR_2$=0.0627 (all data), GOF 1.094. Representative crystallographic data for 2 is presented in Tables 5 and 6.

TABLE 5

Selected bonds (Å) and angles (deg.) for compound (2).

| Pt(1)—N(1) | 1.997(3) | O(1)—C(1) | 1.301(4) |
|---|---|---|---|
| Pt(1)—N(2) | 1.997(3) | N(1)—C(1) | 1.299(4) |
| Pt(1)—As(1) | 2.2687(4) | N(1)—H(1) | 0.8800 |
| Pt(1)—Cl(1) | 2.3361(9) | N(2)—C(4) | 1.305(5) |
| As(1)—O(4) | 1.724(2) | O(3)—As(1)—O(1) | 87.15(12) |
| As(1)—O(3) | 1.742(3) | O(4)—As(1)—O(2) | 89.11(12) |
| As(1)—O(1) | 1.955(3) | O(3)—As(1)—O(2) | 89.99(12) |
| As(1)—O(2) | 1.976(3) | As(1)—Pt(1)—Cl(1) | 177.32(3) |
| As(1)—O(2) | 1.976(3) | O(4)—As(1)—O(3) | 105.48(13) |
| O(2)—C(4) | 1.304(4) | O(4)—As(1)—O(1) | 85.55(11) |
| N(1)—Pt(1)—N(2) | 173.59(13) | O(1)—As(1)—O(2) | 173.05(11) |
| N(1)—Pt(1)—As(1) | 86.22(9) | O(4)—As(1)—Pt(1) | 129.78(10) |
| N(2)—Pt(1)—As(1) | 87.42(9) | O(3)—As(1)—Pt(1) | 124.67(9) |
| N(1)—Pt(1)—Cl(1) | 91.71(9) | O(1)—As(1)—Pt(1) | 93.75(7) |
| N(2)—Pt(1)—Cl(1) | 94.68(9) | O(2)—As(1)—Pt(1) | 93.09(7) |
| | | C(1)—N(1)—Pt(1) | 122.0(3) |

TABLE 6

Hydrogen bonds for compound (2) [Å and deg].

| D—H···A | [ARU] | d(D—H) | d(H···A) | d(D···A) | <DHA |
|---|---|---|---|---|---|
| N(2)—H(2)...O(4) | [3455.01] | 0.88 | 2.23 | 3.077(4) | 163 |
| O(3)—H(3)...Cl(1) | [5665.01] | 0.84 | 2.25 | 3.059(3) | 161 |
| O(4)—H(4)...O(3) | [7645.01] | 0.84 | 1.93 | 2.729(4) | 158 |
| C(2)—H(2B)...Cl(1) | [6555.01] | 0.99 | 2.82 | 3.785(4) | 165 |

Translation of ARU-code to Equivalent Position Code: [7645.] = 3/2 − x, −1/2 + y, z; [5665.] = 1 − x, 1 − y, −z; [3455.] = −1/2 + x, 1/2 − y, −z; [6555.] = 1/2 + x, y, 1/2 − z.

Crystal data for compound (3). $C_5H_{10}AsN_3O_4PtS$, Mr=478.23, Mo—Kα radiation, wavelength 0.71073, T 100(2) K, colorless needle, 0.37×0.08×0.03 mm, orthorhombic, space group Pccn, a=17.1342 (5) Å, b=18.7310 (5) Å, c=6.8347 (2) Å, v=2193.53 (11) Å$^3$, Z=8, $d_{calcd}$=2.896 gcm$^{-3}$, μ=15.976 mm$^{-1}$, F(000)=1760, 35,638 reflections, 3160 unique, $R_{int}$=0.0890, $R_1$=0.0460 [I>2σ(I)], $wR_2$=0.1117 (all data), GOF 1.046. Representative crystallographic data for 3 is presented in Table 7.

TABLE 7

Selected bonds (A) and angles (o) for compound (3).

| Pt1 N1 | 2.036(7) | N2 Pt1 As1 | 88.19(19) |
|---|---|---|---|
| Pt1 N2 | 2.039(7) | N1 Pt1 S1 | 97.4(2) |

TABLE 7-continued

Selected bonds (A) and angles (o) for compound (3).

| Pt1 As1 | 2.2987(9) | N2 Pt1 S1 | 88.6(2) |
|---|---|---|---|
| Pt1 S1 | 2.352(2) | As1 Pt1 S1 | 176.70(6) |
| As1 O3 | 1.720(6) | O3 As1 O4 | 106.6(3) |
| As1 O4 | 1.727(6) | O3 As1 O1 | 88.0(3) |
| As1 O1 | 1.928(6) | O4 As1 O1 | 89.4(3) |
| As1 O2 | 2.084(6) | O3 As1 O2 | 88.0(3) |
| S1 C5 | 1.675(9) | O4 As1 O2 | 88.5(3) |
| O1 C1 | 1.316(10) | O1 As1 O2 | 174.8(2) |
| O2 C3 | 1.284(10) | O3 As1 Pt1 | 125.6(2) |
| N1 C1 | 1.282(12) | O4 As1 Pt1 | 127.8(2) |
| N2 C3 | 1.303(10) | O1 As1 Pt1 | 93.65(18) |
| N3 C5 | 1.162(12) | O2 As1 Pt1 | 91.43(16) |
| N1 Pt1 N2 | 173.9(3) | C5 S1 Pt1 | 104.6(3) |
| N1 Pt1 As1 | 85.8(2) | C3 N2 Pt1 | 120.4(6) |

Example 22

Cell Culture Conditions and In Vitro Cytotoxicity Assay

A. Cell Culture Conditions.

The MDA-MB-231-mCherry breast cancer cells were cultured in Dulbecco's modified Eagle's medium (DMEM) and supplemented with 5% heat-inactivated fetal bovine serum (FBS), 50 units/ml penicillin, 50 μg/ml streptomycin, 2 mM L-glutamine, and 1 μg/ml blasticidin S (Sigma). The A2780 and A2780$^{CP}$ ovarian cancer cell lines and the multiple myeloma RPMI 8226 cell line were cultured in RPMI 1640 medium supplemented with 10% FBS, 50 units/ml penicillin, 50 μg/ml streptomycin, 2 mM L-glutamine. The U-87 and HTC-116 cancer cell lines were cultured without antibiotics. Cells were grown at 37° C. in a humidified atmosphere of 5% of $CO_2$.

B. In Vitro Cytotoxicity Assay for MDA-MB-231mCherry, A270 and A2780CP Cancer Cell Lines.

The cytotoxicities of compound (1), cisplatin, and $As_2O_3$ were assessed by MTS assay using the CellTiter 96 Aqueous MTS (Promega). The 100 μL aliquots of cell suspension (1.0×10$^5$ cells/ml) were plated in 96-well tissue culture plates in the incubator overnight at 37° C. in a humidified atmosphere of 5% of $CO_2$. The serial dilutions of compound (1), cisplatin, and $As_2O_3$ in appropriate media were transferred to the cells. The MTS solution (20 µL) was added after 72 hours and the absorbance was measured at 495 nm 4 hours later. Sigmoidal dose response curves were plotted using the GraphPad Prism software. The $IC_{50}$ values were obtained on at least three independent experiments. In vitro cytotoxicity assay for U-87 and HTC-116 cancer cell line. For the experiment, cells were cultured in RPMI 1640 medium with 5% FBS and 2 mM L-glutamine. The drug was added in similar media supplemented with 50 µg/mL gentamicin. HCT-116 and U-87 cancer cell were plated in 96 well plates. The cells were plated in four replicates. The densities of the cells were 5000 and 10000 per well in 90 µL for HTC-116 and U-87, respectively. Ten microliters (10 µL) of the final drug volume have added per well. The cells were treated with 100, 10, 1, 0.1 0.01, 0.001, 0.0001, 0.00001 and 0.000001 µM of compound (1), cisplatin, and $As_2O_3$. After 48 hours post drug treatment all plates were allowed to equilibrate for 30 minutes at mom temperature from incubator. Addition of 100 µL of Cell Titer Glow (Promega, Fitchburg, Wis.) reagent was added to the wells. The plates were shaken for 2 minutes and allowed to sit for activation prior to reading for 10 minutes. Plates were read on Biotek Synergy H1 (Biotek, Wenooski, Vt.) reader capable of luminescence detection.

TABLE 8

$IC_{50}$ values in µM (±SD) of compound (1), cisplatin, and arsenic trioxide in a panel of different human cancer cell lines

| Cell line | Malignancy | Complex 1 | Cisplatin | $As_2O_3$ |
|---|---|---|---|---|
| A2780 | Ovarian cisplatin sensitive | 20.3 ± 4.0 | 3.1 ± 1.1 | 17.1 ± 1.5 |
| A2780$^{CP}$ | Ovarian cisplatin resistant | 21.4 ± 1.8 | 47.3 ± 2.1 | 21.6 ± 1.4 |
| MDA-MB-231 (mCherry) | Triple negative breast cancer | 9.5 ± 0.1 | 22.3 ± 2.8 | 11.9 ± 2.3 |
| RPMI 8226 | Multiple myeloma | 4.5 ± 1.0 | 1.9 ± 0.1 | 7.1 ± 0.2 |
| HTC-116 | Colon | 1.6 ± 0.4 | 5.5 ± 1.3 | 9.4 ± 0.9 |
| U-87 | Glioblastoma | 0.37 ± 0.11 | 9.6 ± 0.8 | 1.6 ± 2.9 |

Example 23

Orthotopic Cancer Model—Prophetic Example

The anticancer activity of these compounds will be tested for efficacy in triple negative breast cancer, ovarian cisplatin resistant cancer, multiple myeloma, glioblastoma and colon cancer, as well as in other cancers in mouse xenograft models. The mice will be randomized into 4 treatment groups (8 mice per group) as follows: PBS alone, arsenoplatin compounds (4 mg/kg), $As_2O_3$ (4 mg/kg) and cisplatin (4 mg/kg). Stock solutions of arsenic trioxide will be prepared by dissolving solid arsenic trioxide in 5 M NaOH, and the stock solution will be diluted with PBS and pH adjusted to be 7.4. Stock solutions of arsenoplatins and cisplatin will be diluted with PBS. Each group will be treated twice weekly for three weeks by i.p. injections in the case of solid tumors. Tumors will be measured with digital calipers and tumor volume will be calculated using the equation VTumor=$(w2 \times 1 \times \pi)/6$. Mice will be weighted twice weekly.

DEFINITIONS

When introducing elements of aspects of the embodiments, the articles "a," "an," "the," and "said" are intended to mean that there are one or more of the elements. The terms "comprising," "including," and "having" are intended to be inclusive and mean that there may be additional elements other than the listed elements. The word "or" means any one member of a particular list and also includes any combination of members of that list, unless otherwise specified.

The modal verb "may" refers to the preferred use or selection of one or more options or choices among several described embodiments or features contained within the same. Where no options or choices are disclosed regarding a particular embodiment or feature contained in the same, the modal verb "may" refers to an affirmative act regarding how to make or use an aspect of a described embodiment or feature contained in the same, or a definitive decision to use a specific skill regarding a described embodiment or feature contained in the same. In this latter context, the model verb "may" has the same meaning and connotation as the auxiliary verb "can."

The term "about" is used herein to mean approximately, roughly, around, or in the region of. When the term "about" is used in conjunction with a numerical range, it modifies that range by extending the boundaries above and below the numerical values set forth. Preferably, the term "about" is used herein to modify a numerical value above and below the stated value by a variance of 20 percent up or down (higher or lower).

The terms "disclosed compound," "disclosed compounds" and "disclosed compound(s)" refer to one ore more compounds having the structure of formulas (I)-(VII), including species therein.

Not all of the depicted components illustrated or described may be required. In addition, some implementations and embodiments may include additional components. Variations in the arrangement and type of the components may be made without departing from the spirit or scope of the claims as set forth herein. Additional, different or fewer components may be provided and components may be combined. Alternatively or in addition, a component may be implemented by several components.

The above description illustrates the invention by way of example and not by way of limitation. This description clearly enables one skilled in the art to make and use the invention, and describes several embodiments, adaptations, variations, alternatives and uses of the invention, including what is presently believed to be the best mode of carrying out the invention. Additionally, it is to be understood that the invention is not limited in its application to the details of construction and the arrangement of components set forth in the following description or illustrated in the drawings. The invention is capable of other embodiments and of being practiced or carried out in various ways. Also, it will be understood that the phraseology and terminology used herein is for the purpose of description and should not be regarded as limiting.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

The technical effects and technical problems in the specification are exemplary and are not limiting. It should be noted that the embodiments described in the specification may have other technical effects and can solve other technical problems.

What is claimed is:

1. A compound having the structure of formula (I)

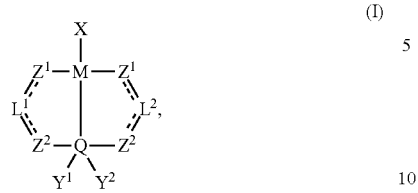

wherein M is Pt, Pd or Ni; Q is As, Sb or Bi; $Z^1$ is N; $Z^2$ is O or S; $L^1$ and $L^2$ are independently C(O), C—$R^1$ or C—$R^2$; X is a Lewis base; $Y^1$ and $Y^2$ are independently selected from —$OR^3$, —$SR^3$ and —$SR^4$, wherein $R^1$ and $R^2$ are independently selected from hydrogen, halogen, cyano, keto, ester, ether, thiol, thioether, thioester, imino, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl, and $C_3$-$C_{15}$ heterocycloalkyl;

wherein $R^3$ and $R^4$ are independently selected from hydrogen, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl, and $C_3$-$C_{15}$ heterocycloalkyl;

wherein the Lewis base can be halogen, N-bonded cyano, nitroso, nitroxyl, N-bonded $C_1$-$C_{10}$ alkyl, alkenyl, N-bonded $C_3$-$C_{10}$ cycloalkyl, N-bonded heteroalkyl, N-bonded $C_1$-$C_{10}$ heteroalkenyl, N-bonded aryl, N-bonded heteroaryl, N-bonded $C_3$-$C_{15}$ heterocycloalkyl, —$NR^5R^6$, N-bonded ligand, S-bonded cyano, sulfonyl, sulfoxyl, thiol, S-bonded thioether, S-bonded thioester, S-bonded $C_1$-$C_{10}$ alkyl, $C_1$-$C_{10}$ alkenyl, S-bonded $C_3$-$C_{10}$ cycloalkyl, S-bonded $C_1$-$C_{10}$ heteroalkyl, S-bonded $C_1$-$C_{10}$ heteroalkenyl, S-bonded aryl, S-bonded heteroaryl, S-bonded $C_3$-$C_{15}$ heterocycloalkyl, —$SR^5$, S-bonded ligand, O-bonded $C_3$-$C_{10}$ cycloalkyl, O-bonded $C_1$-$C_{10}$ heteroalkyl, O-bonded $C_1$-$C_{10}$ heteroalkenyl, O-bonded aryl, O-bonded heteroaryl, O-bonded $C_3$-$C_{15}$ heterocycloalkyl, —$OR^5$, O-bonded carboxylato, O-bonded polycarboxylato, O-bonded ligand, or P-bonded phosphine having formula $P(R^7)_{3-x}(R^8)_x$, where x is 0, 1, 2 or 3;

wherein $R^5$ and $R^6$ are independently selected from hydrogen, O, —$CO_2R^9$, —$COR^9$, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl;

wherein $R^7$ and $R^8$ are independently selected from $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl; and wherein $R^9$ is selected from hydrogen, hydroxyl, halogen, amine, thiol, ether, $C_1$-$C_{10}$alkyl, $C_1$-$C_{10}$ alkenyl, aryl, heteroaryl, $C_3$-$C_{15}$ cycloalkyl and $C_3$-$C_{15}$ heterocycloalkyl.

2. The compound of claim 1, wherein the compound has the structure of formula (II):

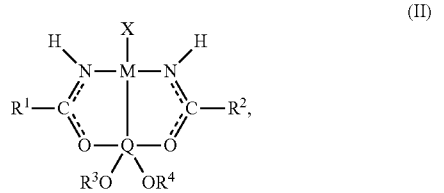

wherein M is Pt, Pd or Ni; Q is As, Sb or Bi; X is a Lewis base;

wherein $R^1$ and $R^2$ are independently selected from hydrogen, halogen, cyano, keto, ester, ether, thiol, thioether, thioester, imino, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl, and $C_3$-$C_{15}$ heterocycloalkyl;

wherein $R^3$ and $R^4$ are independently selected from hydrogen, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl and $C_3$-$C_{15}$ heterocycloalkyl;

wherein the Lewis base can be halogen, N-bonded cyano, nitroso, nitroxyl, N-bonded $C_1$-$C_{10}$ alkyl, alkenyl, N-bonded $C_3$-$C_{10}$ cycloalkyl, N-bonded heteroalkyl, N-bonded $C_1$-$C_{10}$ heteroalkenyl, N-bonded aryl, N-bonded heteroaryl, N-bonded $C_3$-$C_{15}$ heterocycloalkyl, —$NR^5R^6$, N-bonded ligand, S-bonded cyano, sulfonyl, sulfoxyl, thiol, S-bonded thioether, S-bonded thioester, S-bonded $C_1$-$C_{10}$ alkyl, $C_1$-$C_{10}$ alkenyl, S-bonded $C_3$-$C_{10}$ cycloalkyl, S-bonded $C_1$-$C_{10}$ heteroalkyl, S-bonded $C_1$-$C_{10}$ heteroalkenyl, S-bonded aryl, S-bonded heteroaryl, S-bonded $C_3$-$C_{15}$ heterocycloalkyl, —$SR^5$, S-bonded ligand, O-bonded $C_3$-$C_{10}$ cycloalkyl, O-bonded $C_1$-$C_{10}$ heteroalkyl, O-bonded $C_1$-$C_{10}$ heteroalkenyl, O-bonded aryl, O-bonded heteroaryl, O-bonded $C_3$-$C_{15}$ heterocycloalkyl, —$OR^5$, O-bonded carboxylato, O-bonded polycarboxylato, O-bonded ligand, or P-bonded phosphine having formula $P(R^7)_{3-x}(R^8)_x$, where x is 0, 1, 2 or 3;

wherein $R^5$ and $R^6$ are independently selected from hydrogen, O, —$CO_2R^9$, —$COR^9$, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl;

wherein $R^7$ and $R^8$ are independently selected from $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl; and wherein $R^9$ is selected from hydrogen, hydroxyl, halogen, amine, thiol, ether, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl.

3. The compound of claim 1, wherein the compound has the structure of formula (VI):

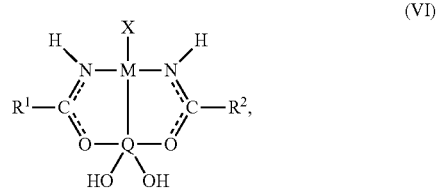

wherein M is Pt, Pd or Ni; Q is As or Sb; X is a Lewis base;

wherein $R^1$ and $R^2$ are independently selected from hydrogen, halogen, cyano, keto, ester, ether, thiol, thioether, thioester, imino, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl, and $C_3$-$C_{15}$ heterocycloalkyl; and wherein the Lewis base can be halogen, N-bonded cyano, nitroso, nitroxyl, N-bonded $C_1$-$C_{10}$ alkyl, alkenyl, N-bonded $C_3$-$C_{10}$ cycloalkyl, N-bonded heteroalkyl, N-bonded $C_1$-$C_{10}$ heteroalkenyl, N-bonded aryl, N-bonded heteroaryl, N-bonded $C_3$-$C_{15}$ heterocycloalkyl, —$NR^5R^6$, N-bonded ligand, S-bonded cyano, sulfonyl, sulfoxyl, thiol, S-bonded thioether, S-bonded thioester, S-bonded $C_1$-$C_{10}$ alkyl, $C_1$-$C_{10}$ alkenyl, S-bonded $C_3$-$C_{10}$ cycloalkyl, S-bonded $C_1$-$C_{10}$ heteroalkyl, S-bonded $C_1$-$C_{10}$ heteroalkenyl, S-bonded aryl, S-bonded heteroaryl, S-bonded $C_3$-$C_{15}$ heterocycloalkyl, —SR⁵, S-bonded ligand, O-bonded $C_3$-$C_{10}$ cycloalkyl, O-bonded $C_1$-$C_{10}$ heteroalkyl, O-bonded $C_1$-$C_{10}$ heteroalkenyl, O-bonded aryl, O-bonded heteroaryl, O-bonded $C_3$-$C_{15}$ heterocycloalkyl, —OR⁵, O-bonded carboxylato, O-bonded polycarboxylato, O-bonded ligand, or P-bonded phosphine having formula $P(R^7)_{3-x}(R^8)_x$, where x is 0, 1, 2 or 3;

wherein $R^5$ and $R^6$ are independently selected from hydrogen, O, —$CO_2R^9$, —$COR^9$, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl;

wherein $R^7$ and $R^8$ are independently selected from $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl; and wherein $R^9$ is selected from hydrogen, hydroxyl, halogen, amine, thiol, ether, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl.

4. The compound of claim 3, wherein the compound is selected from the group consisting of compounds (11)-(19):

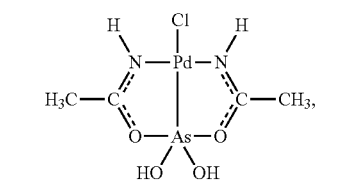
(11)

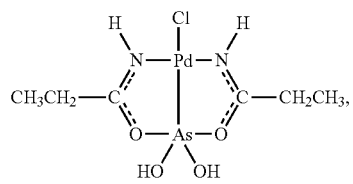
(12)

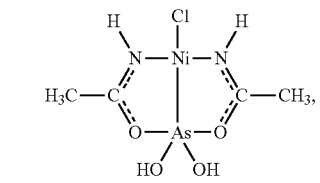
(13)

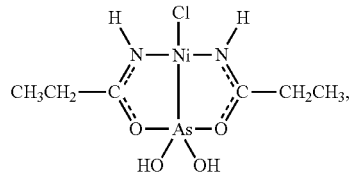
(14)

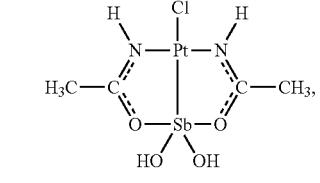
(15)

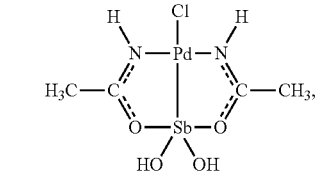
(16)

-continued

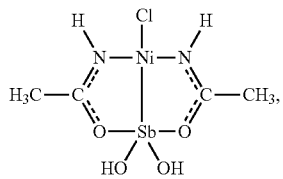
(17)

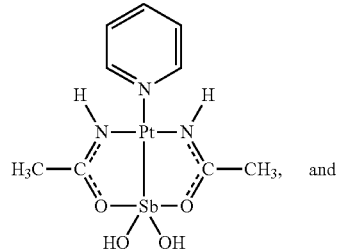
(18)

and

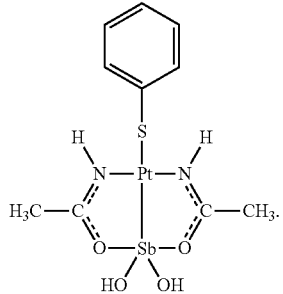
(19)

5. The compound of claim 1, wherein the compound has the structure of formula (VII):

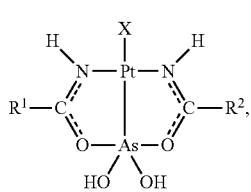
(VII)

wherein X is a Lewis base;

wherein $R^1$ and $R^2$ are independently selected from hydrogen, halogen, cyano, keto, ester, ether, thiol, thioether, thioester, imino, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl, and $C_3$-$C_{15}$ heterocycloalkyl; and wherein the Lewis base can be halogen, N-bonded cyano, nitroso, nitroxyl, N-bonded $C_1$-$C_{10}$ alkyl, $C_1$-$C_{10}$ alkenyl, N-bonded $C_3$-$C_{10}$ cycloalkyl, N-bonded heteroalkyl, N-bonded $C_1$-$C_{10}$ heteroalkenyl, N-bonded aryl, N-bonded heteroaryl, N-bonded $C_3$-$C_{15}$ heterocycloalkyl, —$NR^5R^6$, N-bonded ligand, S-bonded cyano, sulfonyl, sulfoxyl, thiol, S-bonded thioether, S-bonded thioester, S-bonded $C_1$-$C_{10}$ alkyl, $C_1$-$C_{10}$ alkenyl, S-bonded $C_3$-$C_{10}$ cycloalkyl, S-bonded $C_1$-$C_{10}$ heteroalkyl, S-bonded $C_1$-$C_{10}$ heteroalkenyl, S-bonded aryl, S-bonded heteroaryl, S-bonded $C_3$-$C_{15}$ heterocycloalkyl, —SR⁵, S-bonded ligand, O-bonded $C_3$-$C_{10}$ cycloalkyl, O-bonded $C_1$-$C_{10}$ heteroalkyl, O-bonded $C_1$-$C_{10}$ heteroalkenyl, O-bonded aryl, O-bonded heteroaryl, O-bonded $C_3$-$C_{15}$ heterocycloalkyl, —$OR^5$, O-bonded carboxylato, O-bonded polycarboxylato, O-bonded ligand, or P-bonded phosphine having formula $P(R^7)_{3-x}(R^8)_x$, where x is 0, 1, 2 or 3;

wherein $R^5$ and $R^6$ are independently selected from hydrogen, O, —$CO_2R^9$, —$COR^9$, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl;

wherein $R^7$ and $R^8$ are independently selected from $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl; and wherein $R^9$ is selected from hydrogen, hydroxyl, halogen, amine, thiol, ether, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl.

6. The compound of claim 5, wherein the compound is selected from the group consisting of compounds (1)-(10):

(1)
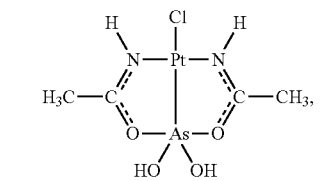

(2)
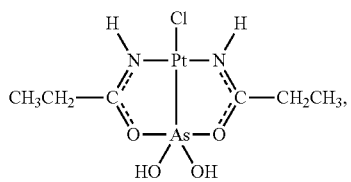

(3)
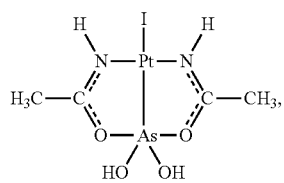

(4)
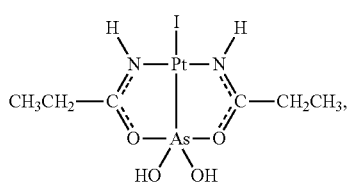

(5)
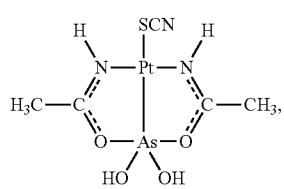

(6)
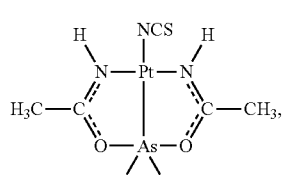

(7)
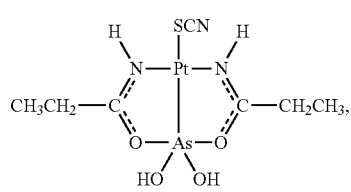

(8)
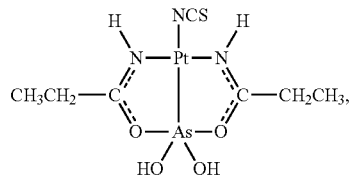

(9)
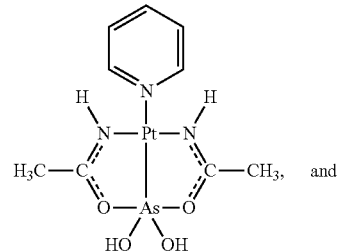

and

(10)
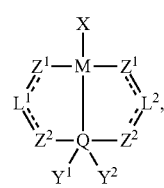

7. A pharmaceutical composition comprising:
an excipient, and
a compound having the structure of formula (I)

(I)

$$\begin{array}{c} X \\ | \\ Z^1\text{—}M\text{—}Z^1 \\ L^1 \diagup \diagdown L^2 \\ Z^2\text{—}Q\text{—}Z^2 \\ | \quad | \\ Y^1 \quad Y^2 \end{array}$$

wherein M is Pt, Pd or Ni; Q is As, Sb or Bi; $Z^1$ is N; $Z^2$ is O or S; $L^1$ and $L^2$ are independently C(O), C—$R^1$ or C—$R^2$; X is a Lewis base; $Y^1$ and $Y^2$ are independently selected from —$OR^3$, —$SR^3$ and —$SR^4$, wherein $R^1$ and $R^2$ are independently selected from hydrogen, halogen, cyano, keto, ester, ether, thiol, thioether, thioester, imino, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl, and $C_3$-$C_{15}$ heterocycloalkyl;

wherein $R^3$ and $R^4$ are independently selected from hydrogen, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl, and $C_3$-$C_{15}$ heterocycloalkyl;

wherein the Lewis base can be halogen, N-bonded cyano, nitroso, nitroxyl, N-bonded $C_1$-$C_{10}$ alkyl, alkenyl, N-bonded $C_3$-$C_{10}$ cycloalkyl, N-bonded heteroalkyl, N-bonded heteroalkenyl, N-bonded aryl, N-bonded heteroaryl, N-bonded $C_3$-$C_{15}$ heterocycloalkyl, —$NR^5R^6$, N-bonded ligand, S-bonded cyano, sulfonyl, sulfoxyl, thiol, S-bonded thioether, S-bonded thioester, S-bonded $C_1$-$C_{10}$ alkyl, $C_1$-$C_{10}$ alkenyl, S-bonded $C_3$-$C_{10}$ cycloalkyl, S-bonded $C_1$-$C_{10}$ heteroalkyl, S-bonded $C_1$-$C_{10}$ heteroalkenyl, S-bonded aryl, S-bonded heteroaryl, S-bonded $C_3$-$C_{15}$ heterocycloalkyl, —$SR^5$, S-bonded ligand, O-bonded $C_3$-$C_{10}$ cycloalkyl, O-bonded $C_1$-$C_{10}$ heteroalkyl, O-bonded $C_1$-$C_{10}$ heteroalkenyl, O-bonded aryl, O-bonded heteroaryl, O-bonded $C_3$-$C_{15}$ heterocycloalkyl, —$OR^5$, O-bonded carboxylato, O-bonded polycarboxylato, O-bonded ligand, or P-bonded phosphine having formula $P(R^7)_{3-x}(R^8)_x$, where x is 0, 1, 2 or 3;

wherein $R^5$ and $R^6$ are independently selected from hydrogen, O, —$CO_2R^9$, —$COR^9$, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl;

wherein $R^7$ and $R^8$ are independently selected from $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl; and wherein $R^9$ is selected from hydrogen, hydroxyl, halogen, amine, thiol, ether, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl.

8. The pharmaceutical composition of claim 7, wherein the compound has the structure of formula (II):

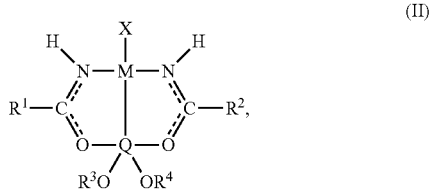

(II)

wherein M is Pt, Pd or Ni; Q is As, Sb or Bi; X is a Lewis base;

wherein $R^1$ and $R^2$ are independently selected from hydrogen, halogen, cyano, keto, ester, ether, thiol, thioether, thioester, imino, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl, and $C_3$-$C_{15}$ heterocycloalkyl;

wherein $R^3$ and $R^4$ are independently selected from hydrogen, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl and $C_3$-$C_{15}$ heterocycloalkyl;

wherein the Lewis base can be halogen, N-bonded cyano, nitroso, nitroxyl, N-bonded $C_1$-$C_{10}$ alkyl, alkenyl, N-bonded $C_3$-$C_{10}$ cycloalkyl, N-bonded heteroalkyl, N-bonded $C_1$-$C_{10}$ heteroalkenyl, N-bonded aryl, N-bonded heteroaryl, N-bonded $C_3$-$C_{15}$ heterocycloalkyl, —$NR^5R^6$, N-bonded ligand, S-bonded cyano, sulfonyl, sulfoxyl, thiol, S-bonded thioether, S-bonded thioester, S-bonded $C_1$-$C_{10}$ alkyl, $C_1$-$C_{10}$ alkenyl, S-bonded $C_3$-$C_{10}$ cycloalkyl, S-bonded $C_1$-$C_{10}$ heteroalkyl, S-bonded $C_1$-$C_{10}$ heteroalkenyl, S-bonded aryl, S-bonded heteroaryl, S-bonded $C_3$-$C_{15}$ heterocycloalkyl, —$SR^5$, S-bonded ligand, O-bonded $C_3$-$C_{10}$ cycloalkyl, O-bonded $C_1$-$C_{10}$ heteroalkyl, O-bonded $C_1$-$C_{10}$ heteroalkenyl, O-bonded aryl, O-bonded heteroaryl, O-bonded $C_3$-$C_{15}$ heterocycloalkyl, —$OR^5$, O-bonded carboxylato, O-bonded polycarboxylato, O-bonded ligand, or P-bonded phosphine having formula $P(R^7)_{3-x}(R^8)_x$, where x is 0, 1, 2 or 3;

wherein $R^5$ and $R^6$ are independently selected from hydrogen, O, —$CO_2R^9$, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl;

wherein $R^7$ and $R^8$ are independently selected from $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl; and wherein $R^9$ is selected from hydrogen, hydroxyl, halogen, amine, thiol, ether, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl.

9. The pharmaceutical composition of claim 7, wherein the compound has the structure of formula (VI):

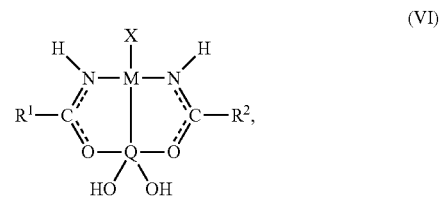

(VI)

wherein M is Pt, Pd or Ni; Q is As or Sb; X is a Lewis base;

wherein $R^1$ and $R^2$ are independently selected from hydrogen, halogen, cyano, keto, ester, ether, thiol, thioether, thioester, imino, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl, and $C_3$-$C_{15}$ heterocycloalkyl; and wherein the Lewis base can be halogen, N-bonded cyano, nitroso, nitroxyl, N-bonded $C_1$-$C_{10}$ alkyl, alkenyl, N-bonded $C_3$-$C_{10}$ cycloalkyl, N-bonded heteroalkyl, N-bonded $C_1$-$C_{10}$ heteroalkenyl, N-bonded aryl, N-bonded heteroaryl, N-bonded $C_3$-$C_{15}$ heterocycloalkyl, —$NR^5R^6$, N-bonded ligand, S-bonded cyano, sulfonyl, sulfoxyl, thiol, S-bonded thioether, S-bonded thioester, S-bonded $C_1$-$C_{10}$ alkyl, $C_1$-$C_{10}$ alkenyl, S-bonded $C_3$-$C_{10}$ cycloalkyl, S-bonded $C_1$-$C_{10}$ heteroalkyl, S-bonded $C_1$-$C_{10}$ heteroalkenyl, S-bonded aryl, S-bonded heteroaryl, S-bonded $C_3$-$C_{15}$ heterocycloalkyl, —$SR^5$, S-bonded ligand, O-bonded $C_3$-$C_{10}$ cycloalkyl, O-bonded $C_1$-$C_{10}$ heteroalkyl, O-bonded $C_1$-$C_{10}$ heteroalkenyl, O-bonded aryl, O-bonded heteroaryl, O-bonded $C_3$-$C_{15}$ heterocycloalkyl, —$OR^5$, O-bonded carboxylato, O-bonded polycarboxylato, O-bonded ligand, or P-bonded phosphine having formula $P(R^7)_{3-x}(R^8)_x$, where x is 0, 1, 2 or 3;

wherein $R^5$ and $R^6$ are independently selected from hydrogen, O, —$CO_2R^9$, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl;

wherein $R^7$ and $R^8$ are independently selected from $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl; and wherein $R^9$ is selected from hydrogen, hydroxyl, halogen, amine, thiol, ether, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl.

10. The pharmaceutical composition of claim 9, wherein the compound is selected from the group consisting of compounds (11)-(19):

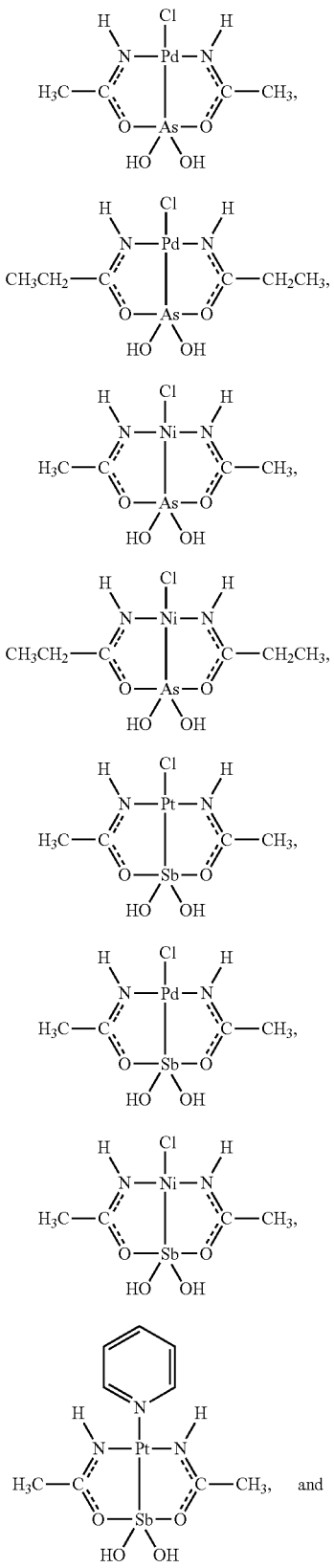

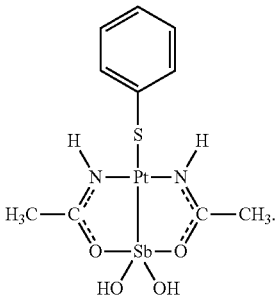

11. The pharmaceutical composition of claim 7, wherein the compound has the structure of formula (VII):

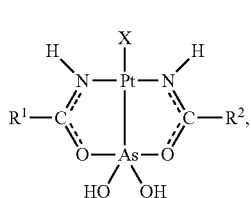

wherein X is a Lewis base;

wherein $R^1$ and $R^2$ are independently selected from hydrogen, halogen, cyano, keto, ester, ether, thiol, thioether, thioester, imino, $C_1$-$C_{10}$ alkyl, $C_1$-$C_{10}$ alkenyl, alkynyl, alkoxyl, amino, amidyl, immino, sulfonyl, sulfoxyl, phosphoryl, phosphoryl ester, glycosyl, aryl, $C_3$-$C_{15}$ cycloalkyl, heteroaryl, and $C_3$-$C_{15}$ heterocycloalkyl; and wherein the Lewis base can be halogen, N-bonded cyano, nitroso, nitroxyl, N-bonded $C_1$-$C_{10}$ alkyl, $C_1$-$C_{10}$ alkenyl, N-bonded $C_3$-$C_{10}$ cycloalkyl, N-bonded heteroalkyl, N-bonded $C_1$-$C_{10}$ heteroalkenyl, N-bonded aryl, N-bonded heteroaryl, N-bonded $C_3$-$C_{15}$ heterocycloalkyl, —$NR^5R^6$, N-bonded ligand, S-bonded cyano, sulfonyl, sulfoxyl, thiol, S-bonded thioether, S-bonded thioester, S-bonded $C_1$-$C_{10}$ alkyl, $C_1$-$C_{10}$ alkenyl, S-bonded $C_3$-$C_{10}$ cycloalkyl, S-bonded $C_1$-$C_{10}$ heteroalkyl, S-bonded $C_1$-$C_{10}$ heteroalkenyl, S-bonded aryl, S-bonded heteroaryl, S-bonded $C_3$-$C_{15}$ heterocycloalkyl, —$SR^5$, S-bonded ligand, O-bonded $C_3$-$C_{10}$ cycloalkyl, O-bonded $C_1$-$C_{10}$ heteroalkyl, O-bonded $C_1$-$C_{10}$ heteroalkenyl, O-bonded aryl, O-bonded heteroaryl, O-bonded $C_3$-$C_{15}$ heterocycloalkyl, —$OR^5$, O-bonded carboxylato, O-bonded polycarboxylato, O-bonded ligand, or P-bonded phosphine having formula $P(R^7)_{3-x}(R^8)_x$, where x is 0, 1, 2 or 3;

wherein $R^5$ and $R^6$ are independently selected from hydrogen, O, —$CO_2R^9$, —$COR^9$, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl;

wherein $R^7$ and $R^8$ are independently selected from $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl; and wherein R⁹ is selected from hydrogen, hydroxyl, halogen, amine, thiol, ether, $C_1$-$C_{10}$ alkyl, $C_1$-$C_{10}$ alkenyl, aryl, heteroaryl, $C_3$-$C_{15}$ cycloalkyl and $C_3$-$C_{15}$ heterocycloalkyl.
12. The pharmaceutical composition of claim 11, wherein the compound is selected from the group consisting of compounds (1)-(10):
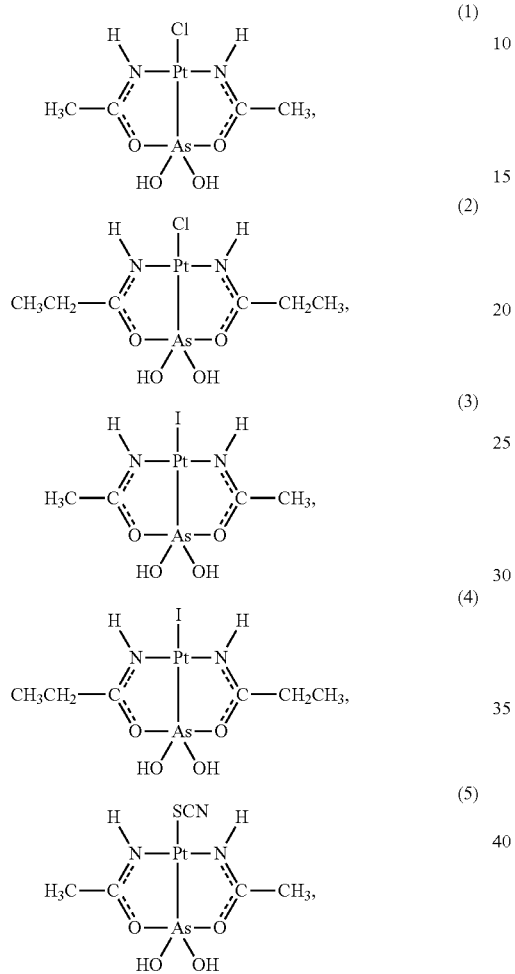
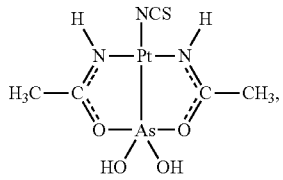
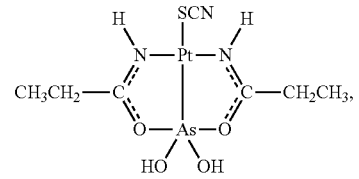
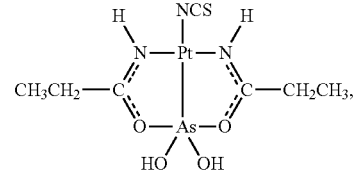
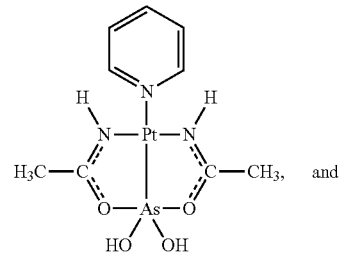
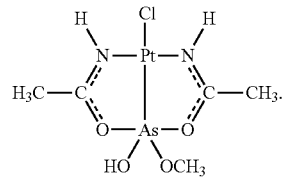
* * * * *